US009834534B2

(12) United States Patent
Withers et al.

(10) Patent No.: US 9,834,534 B2
(45) Date of Patent: *Dec. 5, 2017

(54) NEURAMINIDASE INHIBITOR COMPOUNDS, COMPOSITIONS AND METHODS FOR THE USE THEREOF IN ANTI-VIRAL TREATMENTS

(71) Applicant: THE UNIVERSITY OF BRITISH COLUMBIA, Vancouver (CA)

(72) Inventors: Stephen Withers, Vancouver (CA); Andrew Graham Watts, Bath (GB); Jin Hyo Kim, Suwon-si (KR); Tom Wennekes, Wageningen (NL)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/162,055

(22) Filed: May 23, 2016

(65) Prior Publication Data

US 2017/0022177 A1  Jan. 26, 2017

Related U.S. Application Data

(63) Continuation of application No. 14/533,903, filed on Nov. 5, 2014, now Pat. No. 9,382,284, which is a continuation of application No. 13/354,254, filed on Jan. 19, 2012, now Pat. No. 8,907,111, which is a continuation-in-part of application No. 13/382,284, filed as application No. PCT/CA2010/001063 on Jul. 15, 2010, now Pat. No. 8,815,941.

(60) Provisional application No. 61/213,786, filed on Jul. 15, 2009.

(51) Int. Cl.
| | |
|---|---|
| C07D 309/14 | (2006.01) |
| C07H 13/04 | (2006.01) |
| C07H 13/12 | (2006.01) |
| C07H 15/18 | (2006.01) |
| C07H 1/00 | (2006.01) |
| C07H 13/00 | (2006.01) |
| C07H 15/12 | (2006.01) |
| A61K 31/351 | (2006.01) |
| A61K 31/655 | (2006.01) |

(52) U.S. Cl.
CPC .......... *C07D 309/14* (2013.01); *A61K 31/351* (2013.01); *A61K 31/655* (2013.01); *C07H 1/00* (2013.01); *C07H 13/00* (2013.01); *C07H 13/04* (2013.01); *C07H 13/12* (2013.01); *C07H 15/12* (2013.01); *C07H 15/18* (2013.01)

(58) Field of Classification Search
CPC ..................................................... C07H 15/12
USPC ....................................................... 549/419
See application file for complete search history.

(56) References Cited

U.S. PATENT DOCUMENTS

| | | | |
|---|---|---|---|
| 5,360,817 | A | 11/1994 | Izstein et al. |
| 6,204,029 | B1 | 3/2001 | Withers et al. |
| 6,284,494 | B1 | 9/2001 | Withers et al. |
| 8,815,941 | B2 | 8/2014 | Withers et al. |
| 8,907,111 | B2 | 12/2014 | Withers et al. |
| 9,221,859 | B2 | 12/2015 | Withers et al. |
| 9,382,284 | B2 | 7/2016 | Withers et al. |
| 2014/0350095 | A1 | 11/2014 | Withers et al. |
| 2016/0068501 | A1 | 3/2016 | Withers et al. |

FOREIGN PATENT DOCUMENTS

| | | |
|---|---|---|
| WO | 9523157 | 8/1995 |
| WO | 2004043488 | 5/2004 |
| WO | 2010029302 | 3/2010 |
| WO | 2011006237 | 1/2011 |

OTHER PUBLICATIONS

Buchini et al. (2008) "Towards a New Generation of Specific Trypanosoma cruzi Trans-Sialidase Inhibitors" Angew Chemie Int Ed Engl 47(14):2700-2703.

Carvalho Leonardo J M et al. (2005) "Immunization of Saimiri sciureus monkeys with a recombinant hybrid protein derived from the Plasmodium falciparum antigen glutamate-rich protein and merozoite surface protein 3 can induce partial protection with Freund and montanide ISA720 Adjuvants," Clinical and Diagnostic Laboratory Immunology, 12: 2: 242-248.

Hagiwara, et al. (1994) "Inhibition of Bacterial and Viral Sialidases by 3-Fluoro-N-Acetylneuraminic Acid" Carbohydr Res 263(1):167-172.

Theisen M et al. (2004) IIA Plasmodium falciparum 11-21GLURP-MSP3 chimeric protein; expression in Lactococcus lactis, immunogenicity and induction of biologically active antibodies 11, Vaccine, 22: 9-10:1188-1198.

Amaya et al. (2004) "Structural insights into the catalytic mechanism of Trypanosoma cruzi trans-sialidase" Structure 12(5):775-784.

Bantia et al. (2001) "Comparison of the anti-influenza virus activity of RWJ-270201 with those of oseltamivir and zanamivir" Antimicrob Agents Chemother 45(4):1162-7.

Barrett, S. et al. (2011) PLoS One 6, e23627.

(Continued)

*Primary Examiner* — Taofiq A Solola
(74) *Attorney, Agent, or Firm* — Carol L. Francis; Rudy J. Ng; Bozicevic, Field & Francis LLP

(57) ABSTRACT

Compounds having a structure of Formula I and compositions comprising these compounds are provided. Uses of such compounds and compositions are provided for treatment or prophylaxis of viral infection. In particular, compounds and compositions may be for use in the treatment or prophylaxis of viral influenza.

31 Claims, 8 Drawing Sheets

(56) References Cited

OTHER PUBLICATIONS

Berge et al. (1977) "Pharmaceutical Salts" J. Pharm. Sci. 66(1):1-19.

Cantarel et al. (2009) "The Carbohydrate-Active EnZymes database (CAZy): an expert resource for Glycogenomics" Nucleic Acids Res 37:D233-238.

Chandler et al. (1995) "Synthesis of the Potent Influenza Neuraminidase Inhibitor 4-Guanidino Neu5Ac2en. X-Ray Molecular Structure of 5-Acetamido-4-Amino-2,6-Anhydro-3,4,5-Trideoxy-D-Erythro-L-Gluco-Nononic Acid" J Chem Soc. Perk. Trans 1 9:1173-1180.

Damager et al. (2008) "Kinetic and Mechanistic Analysis of Trypanosoma cruzi Trans-sialidase Reveals a Classical Ping-Pong Mechanism with Acid/Base Catalysis" Biochemistry, 47(11):3507-3512.

Henrissat and Davies (1997) "Structural and sequence-based classification of glycoside hydrolases" Structural Biology 7:637-644.

Ikeda et al. (2004) "2β,3β-Difluorosialic acid derivatives structurally modified at the C-4 position: synthesis and biological evaluation as inhibitors of human parainfluenza virus type 1" Carbohydrate Res. 339(7):1367-72.

Ikeda et al. (2006) "2-Deoxy-2,3-didehydro-N-acetylneuraminic acid analogues structurally modified at the C-4 position: synthesis and biological evaluation as inhibitors of human parainfluenza virus type 1" Bioorg Med Chem 14 (23):7893-7897.

Kim et al (2009) "Development of New and Selective Trypanosoma cruzi trans-Sialidase Inhibitors from Sulfonamide Chalcones and their Derivatives" ChemBioChem 10:2475-2479.

Leneva et al. (2001) "Efficacy of zanamivir against avian influenza A viruses that possess genes encoding H5NI Internal proteins and are pathogenic in mammals" Antimicrob Agents Chemother 45(4):1216-24.

Morley et al. (2009) "Bacteriophage KIF Endo-Sialidase is an Inverting Glycosidase" The Journal of Biological Chemistry 284:17404-17410.

Newstead et al. (2008) "The structure of Clostridium perfringens NanI sialidase and its catalytic intermediates" J. Biol Chem 283:9080-9088.

Tisdale (2000) "Monitoring of viral susceptibility: new challenges with the development of influenza NA inhibitors" Rev Med Viral 10(1):45-55.

Von Itzstein, M. et al. (1993) "A convenient method for the introduction of nitrogen and sulfur at C-4 on a sialic acid analogue" Carbohydr. Res. 244(1): 181-185.

Von Itzstein (2007) "The war against influenza: discovery and development of sialidase inhibitors" Nat Rev Drug Discov 6(12):967-974.

Watts et al (2003) "Trypanosoma cruzi Trans-sialidase Operates through a Covalent Sialyl-Enzyme Intermediate: Tyrosine Is the Catalytic Nucleophile" J. Am. Chem. Soc. 125:7532-7533.

Watts and Withers (2004) "The synthesis of some mechanistic probes for sialic acid processing enzymes and the labeling of a sialidase from Trypanosoma rangeli" Can_ J. Chem. 82:1581-1588.

Watts et al. (2006) "Structural and Kinetic Analysis of Two Covalent Sialosyl-Enzyme Intermediates on Trypanosoma rangeli Sialidase" J Biol Chem 281:4149-4155.

Withers & Aebersold (1995) "Approaches to labeling and identification of active site residues in glycosidases" Protein Sci 4(3):361-372.

Zbiral et al. (1989) "Synthesis of the 4-acetamido-4-deoxy analogue of N-acetylneuraminic acid and its behaviour towards CMP-sialate synthase" Carbohydr Res 194:C I5-C18.

NEURAMINIDASE INHIBITOR COMPOUNDS, COMPOSITIONS AND METHODS FOR THE USE THEREOF IN ANTI-VIRAL TREATMENTS

CROSS REFERENCE TO RELATED APPLICATIONS

This application is a continuation of U.S. application Ser. No. 14/533,903, filed Nov. 5, 2014, which is a continuation of U.S. application Ser. No. 13/354,254, filed Jan. 19, 2012, which is a continuation-in-part application of U.S. application Ser. No. 13/382,284, filed Jul. 15, 2010, entitled "NEURAMINIDASE INHIBITOR COMPOUNDS, COMPOSITIONS AND METHODS FOR THE USE THEREOF AS ANTI-VIRALS", which application is a §371 application of PCT/CA2010/001063, filed Jul. 15, 2010, which application claims priority benefit of U.S. Provisional Patent Application Ser. No. 61/213,786, filed Jul. 15, 2009, each of which applications is incorporated herein by reference in its entirety.

TECHNICAL FIELD

This invention relates to therapeutics, their uses and methods for the treatment or prophylaxis of viral infection. In particular the invention relates to compounds, compositions, therapies, and methods of treatment for viral infections such as influenza.

BACKGROUND

Infection and invasion by influenza viruses requires the intermediacy of sialic acid residues on the surface of the host cell. Sialic acid and neuraminic acid are used interchangeably. Similarly, sialidase and neuraminidase are used interchangeably. Initial attachment of the virus to the host cell occurs via the binding of the virus to these sialic acids (charged, 9-carbon sugars) through the hemagglutinin protein of the virus. Once inside the cell the virus replicates by taking advantage of the host cellular machinery. However, in order to remain optimally infective, the virus has evolved a neuraminidase that cuts off the sialic acid from the host cell surface to assist the virus in escaping the host cell to infect other cells. Failure to cut off the sialic acid from the host cell surface, results in retention of virus through attachment to the host cell.

The GH33 family of neuraminidases contains all the sialidases except the viral enzymes (GH34 family). The GH33 and GH34 families are distinct structurally and by sequence (See Cantarel B L. et al. (2009); and Henrissat B. and Davies G J (1997) for background on Family classifications). Previous work has demonstrated that 2,3-difluoro-sialic acids are effective inhibitors of GH33 neuraminidases and that GH33 neuraminidases proceed through a covalent intermediate (see for example, Watts, A. et al. (2003); Amaya, M. F. et al. (2004); Watts, A. G. and Withers, S. G. (2004); Watts, A. G. et al. (2006); Newstead, S. et al. (2008); Damager, I. et al. (2008); and Buchini, S. et al. (2008)).

The most probable mechanism for the GH34 sialidase (i.e. viral sialidases) reported in the literature is one involving an ion-pair intermediate (von Itzstein M. (2007)).

A number of compounds are known to inhibit neuraminidases. Some well known neuraminidase inhibitors are alkene containing sialic acid analogues (for example: Laninamivir CAS #203120-17-6; Oseltamivir (Tamiflu) CAS #204255-11-8; and Zanamivir (Relenza) CAS #139110-80-8; see also U.S. Pat. No. 5,360,817; and Ikeda et al. Bioorganic & Medicinal Chemistry (2006) 14:7893-7897). Fluorinated sugar derivatives with (reactive) fluoride leaving groups have been shown to be inhibitors of a range of "retaining" glycosidases and function via formation of particularly stable glycosyl-enzyme intermediates (for example, Hagiwara et al. (1994); and Buchini et al. (2008)). These reagents are quite specific with respect to their target enzymes, have been shown to be highly bio-available, and even capable of crossing the blood-brain barrier. Such inhibitors are mechanism-based in their action, making the development of resistance by viruses difficult, whereby any mutations in the viral enzyme that reduce the inhibition must necessarily reduce the efficiency of the enzyme on the natural substrate, sialic acid and therefore less likely to be tolerated.

SUMMARY

This invention is based in part on the fortuitous discovery that compounds having a covalent intermediate, as described herein, modulate neuraminidase. Specifically, compounds identified herein, show inhibition of neuraminidase, which may be useful for the treatment or prophylaxis of viral infection. In particular, the treatment or prophylaxis of influenza.

The compounds described herein may be used for in vivo or in vitro research uses (i.e. non-clinical) to investigate the mechanisms of neuraminidase inhibition. Furthermore, these compounds may be used individually or as part of a kit for in vivo or in vitro research to investigate neuraminidase inhibition using recombinant proteins, viral strains, cells maintained in culture, and/or animal models. Alternatively, the compounds described herein may be combined with commercial packaging and/or instructions for use.

This invention is also based in part on the discovery that the compounds described herein, may also be used to modulate neuraminidase activity either in vivo or in vitro for both research and therapeutic uses. The compounds may be used in an effective amount so that neuraminidase activity may be modulated. The neuraminidase may be viral. The neuraminidase may be an influenza neuraminidase. In particular, the compounds may be used to inhibit neuraminidase activity. The compounds modulatory activity may be used in either an in vivo or an in vitro model for the study of viral infection. For example, influenza infection. Furthermore, the compounds modulatory activity may be used for the treatment or prophylaxis of viral infection. The viral infection may be influenza.

Furthermore, this invention is based in part on the appreciation that 3-fluoro-sialic acids compounds may be GH34 sialidase inhibitors provided that the compounds have a sufficient leaving group at carbon 2 (position Z in Formula I) in addition to the appropriate stereochemistry, as described herein. Compounds identified herein, show inhibition of neuraminidase, which may be useful for the treatment or prophylaxis of viral infection. In particular the treatment or prophylaxis of influenza.

In accordance with one embodiment, there are provided compounds having a structure of Formula I:

I wherein
T is OH, C(O)NH$_2$, COOH or COOR$^1$,
  wherein R$^1$ is a C$_{1-20}$ linear, branched or cyclic, saturated or unsaturated, optionally substituted alkyl group,
    wherein the optional substituent is selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S;
Z is COOMe, F, Cl, Br, or OSO$_2$R$^2$,
  wherein R$^2$ is a C$_{1-20}$ linear, branched or cyclic, saturated or unsaturated, optionally substituted alkyl group,
    wherein the optional substituent is selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S;
A is selected from the group including of: H, F, Cl, Br, OH, CN, OR$^3$, NO$_2$, SO$_2$R$^3$, SR$^3$ and COR$^3$,
  wherein R$^3$ is a C$_{1-20}$ linear, branched or cyclic, saturated or unsaturated, optionally substituted alkyl group,
    wherein the optional substituent is selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S;
D may be selected from the group including of: H, F, Cl, Br, OH, CN, OR$^4$, NO$_2$, SO$_2$R$^4$, SR$^4$ and COR$^4$, provided A and D may be not both H, and
  wherein R$^4$ may be a C$_{1-20}$ linear, branched or cyclic, saturated or unsaturated, optionally substituted alkyl group,
    wherein the optional substituent may be selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S;
collectively, A and D, optionally form an oxo group;
X may be selected from the group including of: N$_3$, NH$_2$, NHR$^5$, NHCH$_3$, NHCH$_2$CH$_3$, NHC(NH)NH$_2$, NHC(NH)NHR$^5$, NR$^5$R$^6$, and NHC(NH)N(R$^5$)R$^6$,
  wherein R$^5$ and R$^6$ may be independently C$_6$H$_5$, CH$_2$C$_6$H$_5$ or a C$_{1-8}$ alkyl group;
E may be selected from the group including of: NH$_2$, NHC(O)CH$_3$, OR$^7$, NHR$^7$ and N(R$^7$)(R$^8$),
  wherein R$^7$ and R$^8$ may be independently a C$_{1-20}$ linear, branched or cyclic, saturated or unsaturated, optionally substituted alkyl group,
    wherein the optional substituent may be selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S;
Q may be selected from the group including of: CH$_2$OH, CH$_2$R$^9$, CH(R$^9$)(R$^{10}$), C(R$^9$)(R$^{10}$)(R$^{11}$),

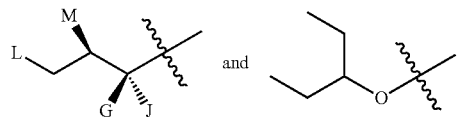

wherein
R$^9$, R$^{10}$ and R$^{11}$ may be independently CH$_3$ or CH$_2$CH$_3$, and
each of J and G may be independently selected from the group: H, OH, OAc, OC(O)CH$_3$, F, Cl, Br, NO$_2$, CN, OR$^{12}$, SO$_2$R$^{12}$, COR$^{12}$ and SR$^{12}$,
  wherein R$^{12}$ may be CH$_3$, CH$_2$CH$_3$ or CH$_2$CH$_2$CH$_3$, and
M may be H, OH, OAc, OC(O)CH$_3$, NH$_2$, F or Cl, and
L may be H, OH, OAc, OC(O)R$^{13}$ or NH$_2$,
  wherein R$^{13}$ may be a C$_{1-20}$ linear, branched or cyclic, saturated or unsaturated, optionally substituted alkyl group,
    wherein the optional substituent may be selected from one or more of the group: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S.

In accordance with a further embodiment, there are provided compounds having a structure of formula I:

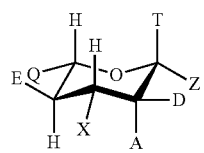

wherein
T may be C(O)NH$_2$, COOH or COOR$^1$,
  wherein R$^1$ may be a C$_{1-20}$ linear, branched or cyclic, saturated or unsaturated, optionally substituted alkyl group,
    wherein the optional substituent may be selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S;
Z may be F, Cl, Br, or OSO$_2$R$^2$,
  wherein R$^2$ may be a C$_{1-20}$ linear, branched or cyclic, saturated or unsaturated, optionally substituted alkyl group,
    wherein the optional substituent may be selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S;
A may be F or Cl;
D may be H;
X may be selected from the group including of: NH$_2$, NHCH$_3$, NHCH$_2$CH$_3$, NHCH$_2$CH$_2$CH$_3$, NHCH$_2$CH$_2$CH$_2$CH$_3$, and NHC(NH)NH$_2$;

E may be $NH_2$ or $NHC(O)CH_3$;

Q may be selected from the group including of:

wherein
each of J and G may be independently selected from the group: H, OH, OAc, $OC(O)CH_3$, F, Cl, Br, $NO_2$, CN, $OR^{12}$, $SO_2R^{12}$, $COR^{12}$ and $SR^{12}$,
wherein $R^{12}$ may be $CH_3$, $CH_2CH_3$ or $CH_2CH_2CH_3$, and M may be H, OH, OAc, $OC(O)CH_3$, $NH_2$, F or Cl, and L may be H, OH, OAc, $OC(O)R^{13}$ or $NH_2$,
wherein $R^{13}$ may be a $C_{1-10}$ linear, branched or cyclic, saturated or unsaturated, optionally substituted alkyl group,
wherein the optional substituent may be selected from one or more of the group: oxo, OH, F, Cl, Br, I, $NH_2$, CN, SH, $SO_3H$ and $NO_2$, and
wherein zero to ten backbone carbons of the optionally substituted alkyl group may be optionally and independently substituted with O, N or S.

In accordance with a further embodiment, there are provided compounds having a structure of formula I:

I wherein
T may be $C(O)NH_2$, COOH or $COOR^1$,
wherein $R^1$ may be a $C_{1-20}$ linear, branched or cyclic, saturated or unsaturated, optionally substituted alkyl group,
wherein the optional substituent may be selected from one or more of the group including of: oxo, OH, F, Cl, Br, I, $NH_2$, CN, SH, $SO_3H$ and $NO_2$, and
wherein zero to ten backbone carbons of the optionally substituted alkyl group may be optionally and independently substituted with O, N or S;

Z may be F or Cl;
A may be F or Cl;
D may be H;
X may be selected from the group including of: $NH_2$, $NHCH_3$, $NHCH_2CH_3$, $NHCH_2CH_2CH_3$, $NHCH_2CH_2CH_2CH_3$, and $NHC(NH)NH_2$;
E may be $NH_2$ or $NHC(O)CH_3$;

Q may be selected from the group including of:

wherein
each of J and G may be independently selected from the group: H, OH, OAc, $OC(O)CH_3$, F, Cl, Br, $NO_2$, CN,
M may be H, OH, OAc; and
L may be H, OH, OAc.

In accordance with a further embodiment, there are provided compounds as described herein for modulating viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there are provided compounds as described herein for use in the preparation of a medicament for modulating viral neuraminidase activity.

The viral neuraminidase may be a GH34 neuraminidase. The modulating of viral neuraminidase activity may be for the treatment of influenza in an animal. The animal may be a mammal. The animal may be a human.

In accordance with a further embodiment, there are provided compounds as described herein for modulating viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there are provided pharmaceutical compositions which may include one or more compounds as described herein and a pharmaceutically acceptable excipient. The viral neuraminidase may be a GH34 neuraminidase. The modulating of viral neuraminidase activity may be for the treatment of influenza in an animal. The animal may be a mammal. The animal may be a human.

In accordance with a further embodiment, there are provided compounds or pharmaceutically acceptable salts thereof as described herein for modulating viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there is provided a method of modulating viral neuraminidase activity with one or more compounds described herein or a pharmaceutically acceptable salt thereof. The viral neuraminidase may be a GH34 neuraminidase. The modulating of viral neuraminidase activity may be for the treatment of influenza in an animal. The animal may be a mammal. The animal may be a human.

In accordance with a further embodiment, there is provided a commercial package which may contain one or more compounds described herein or a pharmaceutically acceptable salt thereof or a pharmaceutical composition thereof. The commercial package may optionally contain instructions for the use of the compounds or pharmaceutically acceptable salt thereof or pharmaceutical composition thereof in the treatment of influenza.

T may be C(O)NH$_2$, COOH or COOR$^1$, wherein R$^1$ may be a C$_{1-20}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$. Alternatively, T may be C(O)OCH$_3$, C(O)OCH$_2$CH$_3$, C(O)OCH$_2$CH$_2$CH$_3$, C(O)OCH$_2$CH$_2$CH$_2$CH$_3$, C(O)OCH$_2$CH$_2$CH$_2$CH$_2$CH$_3$, C(O)OCH$_2$CH$_2$CH$_2$CH$_2$CH$_2$CH$_3$, C(O)OCH$_2$CH$_2$CH$_2$CH$_2$CH$_2$CH$_2$CH$_3$, C(O)OCH$_2$CH$_2$CH$_2$CH$_2$CH$_2$CH$_2$CH$_2$CH$_3$, or COOH. Alternatively, T may be C(O)OCH$_3$, C(O)OCH$_2$CH$_3$, C(O)OCH$_2$CH$_2$CH$_3$, C(O)OCH$_2$CH$_2$CH$_2$CH$_3$, C(O)OCH$_2$CH$_2$CH$_2$CH$_2$CH$_3$, or COOH.

A may be selected from the group including of: F, Cl, Br, OH, CN, OR$^3$, NO$_2$, and COR$^3$, wherein R$^3$ may be a C$_{1-20}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S. Alternatively, A may be selected from the group including of: F, Cl, Br, OH, CN, OR$^3$, and NO$_2$, wherein R$^3$ may be a C$_{1-20}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S. Alternatively, A may be selected from the group including of: F, Cl, Br, OH, CN, and NO$_2$. Alternatively, A may be selected from the group including of: F, Cl, Br, OR$^3$, and NO$_2$, wherein R$^3$ may be a C$_{1-20}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$. Alternatively, A may be selected from the group including of: F, Cl, and OR$^3$, wherein R$^3$ may be a C$_{1-20}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$. Alternatively, A may be F, Cl. Alternatively, A may be F.

D may be selected from the group including of: H, F, Cl, Br, OH, CN, OR$^4$, NO$_2$, and COR$^4$, provided A and D may be not both H, and wherein R$^4$ may be a C$_{1-10}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S. Alternatively, D may be selected from the group including of: H, F, Cl, Br, OH, CN, OR$^4$, NO$_2$, and COR$^4$, provided A and D may be not both H, and wherein R$^4$ may be a C$_{1-10}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$. Alternatively, D may be selected from the group including of: H, F, Cl, Br, OH, CN, and NO$_2$, provided A and D may be not both H. Alternatively, D may be selected from the group including of: H, F, Cl, Br, OH and NO$_2$, provided A and D may be not both H. Alternatively, D may be selected from the group including of: H, F, Cl, Br, and OH, provided A and D may be not both H. Alternatively, D may be selected from the group including of: H, F, Cl, and Br, provided A and D may be not both H. Alternatively, D may be selected from the group including of: H, F, and Cl, provided A and D may be not both H. Alternatively, D may be selected from the group including of: H, F, and Cl, provided A and D may be not both H. Alternatively, D may be F or Cl. Alternatively, D may be H, or F, provided A and D may be not both H. Alternatively, D may be F. Alternatively, D may be H, provided A and D may be not both H.

X may be selected from the group including of: NH$_2$, NHR$^5$, NHCH$_3$, NHCH$_2$CH$_3$, NHC(NH)NH$_2$, NHC(NH)NHR$^5$, and NR$^5$R$^6$, wherein R$^5$ and R$^6$ may be independently C$_6$H$_5$, CH$_2$C$_6$H$_5$ or a C$_{1-8}$ alkyl group. Alternatively, X may be selected from the group including of: NH$_2$, NHR$^5$, NHCH$_3$, NHCH$_2$CH$_3$, NHC(NH)NH$_2$, and NHC(NH)NHR$^5$, wherein R$^5$ may be C$_6$H$_5$, CH$_2$C$_6$H$_5$ or a C$_{1-8}$ alkyl group. Alternatively, X may be selected from the group including of: NH$_2$, NHR$^5$, NHCH$_3$, NHCH$_2$CH$_3$, and NHC(NH)NH$_2$, wherein R$^5$ may be C$_6$H$_5$, CH$_2$C$_6$H$_5$ or a C$_{1-8}$ alkyl group. Alternatively, X may be selected from the group including of: NH$_2$, NHR$^5$, NHCH$_3$, NHCH$_2$CH$_3$, and NHC(NH)NH$_2$, wherein R$^5$ may be C$_6$H$_5$, CH$_2$C$_6$H$_5$ or a C$_{1-8}$ alkyl group. Alternatively, X may be selected from the group including of: NH$_2$, NHR$^5$, NHCH$_3$, NHCH$_2$CH$_3$, and NHC(NH)NH$_2$, wherein R$^5$ may be a C$_{1-8}$ alkyl group. Alternatively, X may be selected from the group including of: NH$_2$, NHCH$_3$, and NHC(NH)NH$_2$. Alternatively, X may be selected from the group including of: NH$_2$, NHCH$_2$CH$_3$, and NHC(NH)NH$_2$. Alternatively, X may be NH$_2$ or NHC(NH)NH$_2$.

E may be selected from the group including of: NH$_2$, NHC(O)CH$_3$, OR$^7$, NHR$^7$, wherein R$^7$ may be independently a C$_{1-10}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$, and wherein zero to ten backbone carbons of the optionally substituted alkyl group may be optionally and independently substituted with O, N or S. Alternatively, E may be selected from the group including of: NH$_2$, NHC(O)CH$_3$, OR$^7$, and NHR$^7$, wherein R$^7$ may be independently a C$_{1-10}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$. Alternatively, E may be selected from the group including of: NH$_2$, NHC(O)CH$_3$, and OR$^7$, wherein R$^7$ may be independently a C$_{1-10}$ linear, branched or cyclic, saturated or unsaturated, optionally substituted alkyl group, wherein the optional substituent may be selected from one or more of the group including of: oxo, OH, F, Cl, Br, I, NH$_2$, CN, SH, SO$_3$H and NO$_2$. Alternatively, E may be NH$_2$ or NHC(O)CH$_3$. Alternatively, E may be NHC(O)CH$_3$.

Q may be selected from the group including of: CH$_2$R$^9$, CH(R$^9$)(R$^{10}$), C(R$^9$)(R$^{10}$)(R$^{11}$),

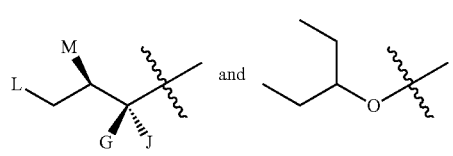

wherein $R^9$, $R^{10}$ and $R^{11}$ may be independently $CH_3$ or $CH_2CH_3$, and each of J and G may be independently selected from the group: H, OH, OAc, $OC(O)CH_3$, F, Cl, Br, $NO_2$, CN, $OR^{12}$, $SO_2R^{12}$, $COR^{12}$ and $SR^{12}$, wherein $R^{12}$ may be $CH_3$, $CH_2CH_3$ or $CH_2CH_2CH_3$, and M may be H, OH, OAc, $OC(O)CH_3$, $NH_2$, F or Cl, and L may be H, OH, OAc, $OC(O)R^{13}$ or $NH_2$, wherein $R^{13}$ may be a $C_{1-20}$ linear, branched or cyclic, saturated or unsaturated, optionally substituted alkyl group, and wherein the optional substituent may be selected from one or more of the group: oxo, OH, F, Cl, Br, I, $NH_2$, CN, SH, $SO_3H$ and $NO_2$. Alternatively, Q may be selected from the group including of:

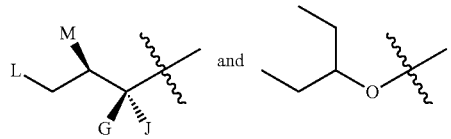

each of J and G may be independently selected from the group: H, OH, OAc, $OC(O)CH_3$, F, Cl, Br, $NO_2$, CN, M may be H, OH, OAc, $OC(O)CH_3$, $NH_2$, F or Cl, and L may be H, OH, OAc, $OC(O)R^{13}$ or $NH_2$. Alternatively, Q may be selected from the group including of:

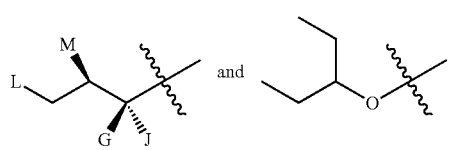

each of J and G may be independently selected from the group: H, OH, OAc, M may be H, OH, or OAc, and L may be H, OH, or OAc. Alternatively, Q may be:

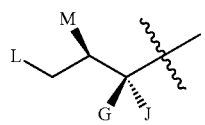

each of J and G may be independently selected from the group: H, OH, OAc, M may be H, OH, or OAc, and L may be H, OH, or OAc. Alternatively, Q may be:

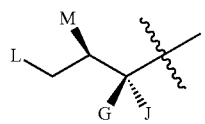

each of J and G may be independently selected from the group: OH, OAc, M may be OH, or OAc, and L may be OH, or OAc.

In accordance with a further embodiment, there is provided a method of preparing compound 2:

the method including: reacting a compound SAN3:

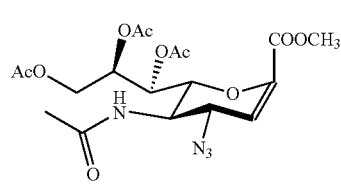

with Selectfluor in the presence of $MeNO_2/H_2O$ for at least 4 days to form compound 1:

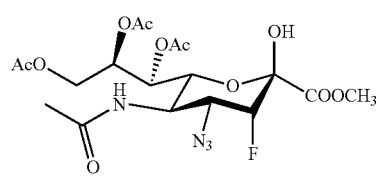

and reacting compound 1 with diethylaminosulfur trifluoride (DAST), $CH_2CL_2$ at between −30° C.-0° C.

The method may further include: mixing compound 2 with NaOMe and MeOH; then mixing with Pd/C, $H_2$, and MeOH; and then mixing with LiOH, $H_2O$, and MeOH to form compound 4:

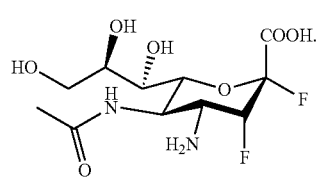

In accordance with a further embodiment, there is provided a method of preparing compound 12, the method may include mixing compound 2:

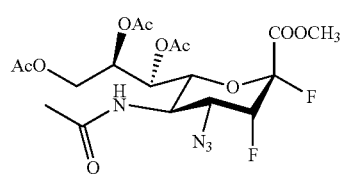

with NaOMe and MeOH; then mixing with AcOH until neutral; then mixing with $PMe_3$, $H_2O$, and MeOH; and then reacting with compound VII:

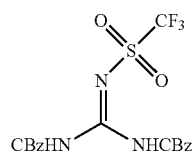

in $Et_3N$, MeOH, and DMF to produce compound VIII:

VIII

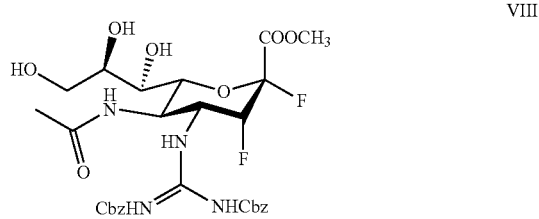

then reacting compound VIII with LiOH, $H_2O$, and THF; and then reacting with Pd/C, $H_2$, $H_2O$, and THF.

In accordance with a further embodiment, there are provided compounds which may be selected from one or more of the compounds set out in TABLES 2A and 2B.

DETAILED DESCRIPTION

Figure 1:
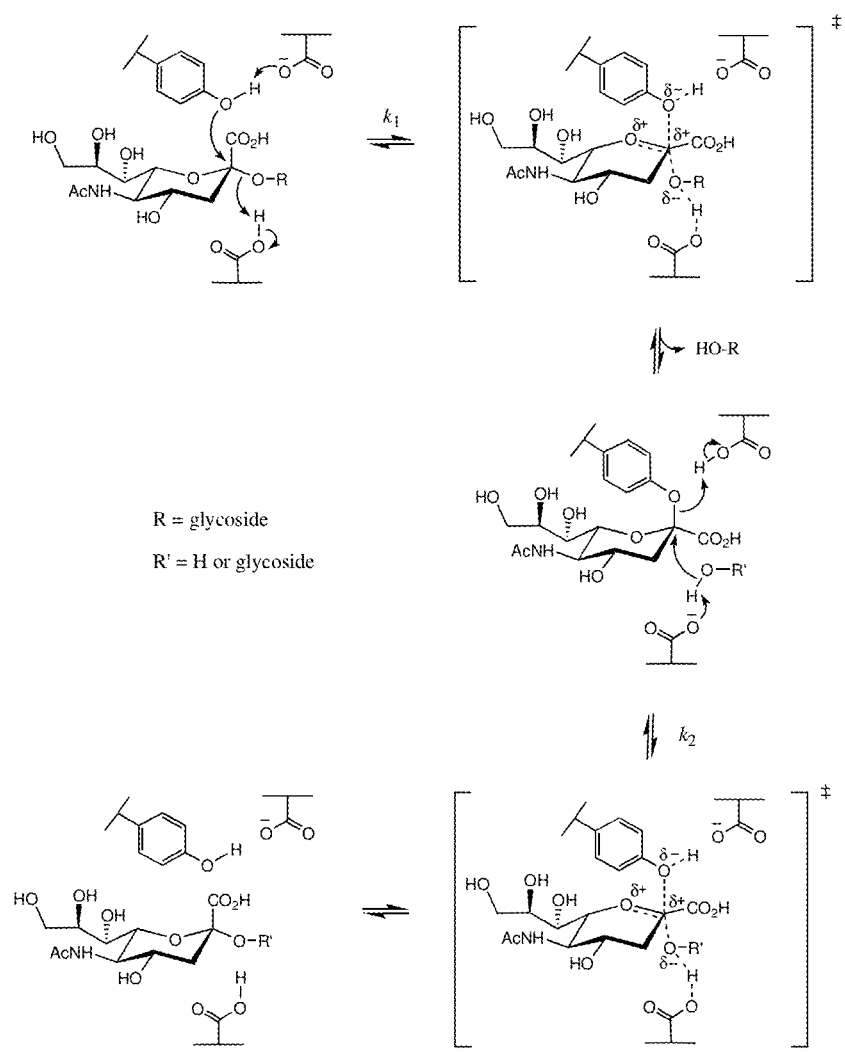
FIG. 1 shows a neuraminidase mechanism.

As used herein, the phrase "$C_{x-y}$ alkyl" or "$C_x$-$C_y$ alkyl" is used as it is normally understood to a person of skill in the art and often refers to a chemical entity that has a carbon skeleton or main carbon chain comprising a number from x to y (with all individual integers within the range included, including integers x and y) of carbon atoms. For example a "$C_{1-10}$ alkyl" is a chemical entity that has 1, 2, 3, 4, 5, 6, 7, 8, 9 or 10 carbon atom(s) in its carbon skeleton or main chain.

As used herein, the term "branched" is used as it is normally understood to a person of skill in the art and often refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl are tert-butyl and isopropyl.

As used herein, the term "unbranched" is used as it is normally understood to a person of skill in the art and often refers to a chemical entity that comprises a skeleton or main chain that does not split off into more that one contiguous chain. Non-limiting examples of unbranched alkyls are methyl, ethyl, n-propyl, and n-butyl.

As used herein, the term "substituted" is used as it is normally understood to a person of skill in the art and often refers to a chemical entity that has one chemical group replaced with a different chemical group that contains one or more heteroatoms. Unless otherwise specified, a substituted alkyl is an alkyl in which one or more hydrogen atom(s) is/are replaced with one or more atom(s) that is/are not hydrogen(s). For example, chloromethyl is a non-limiting example of a substituted alkyl, more particularly an example of a substituted methyl. Aminoethyl is another non-limiting example of a substituted alkyl, more particularly it is a substituted ethyl. The functional groups described herein may be substituted with, for example, and without limitation, 1, 2, 3, 4, 5, 6, 7, 8, 9 or 10 substituents.

As used herein, the term "unsubstituted" is used as it is normally understood to a person of skill in the art and often refers to a chemical entity that is a hydrocarbon and/or does not contain a heteroatom. Non-limiting examples of unsubstituted alkyls include methyl, ethyl, tert-butyl, and pentyl.

As used herein, the term "saturated" when referring to a chemical entity is used as it is normally understood to a person of skill in the art and often refers to a chemical entity that comprises only single bonds. Non-limiting examples of saturated chemical entities include ethane, tert-butyl, and $N^+H_3$.

As used herein the term "halogenated" is used as it would normally be understood to a person of skill in the art and refers to a moiety or chemical entity in which a hydrogen atom is replaced with a halogen atom such as chlorine, fluorine, iodine or bromine. For example, a fluorinated side chain refers to a side chain wherein one or more hydrogen atoms is replaced with one or more fluorine atoms.

Non-limiting examples of saturated $C_1$-$C_{10}$ alkyl may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{10}$ alkenyl may include vinyl, allyl, isopropenyl, 1-propene-2-yl, 1-butene-1-yl, 1-butene-2-yl, 1-butene-3-yl, 2-butene-1-yl, 2-butene-2-yl, octenyl and decenyl. Non-limiting examples of $C_2$-$C_{10}$ alkynyl may include ethynyl, propynyl, butynyl, pentynyl, hexynyl, heptynyl, octynyl, nonynyl and decynyl. Saturated $C_1$-$C_{10}$ alkyl, $C_2$-$C_{10}$ alkenyl or $C_2$-$C_{10}$ alkynyl may be, for example, and without limitation, interrupted by one or more heteroatoms which are independently nitrogen, sulfur or oxygen.

Non-limiting examples of the $C_6$-$C_{10}$ aryl group may include phenyl (Ph), pentalenyl, indenyl, naphthyl, and azulenyl. The $C_{6-9}$ aryl-$C_{1-4}$ alkyl group may be, for example, and without limitation, a $C_{1-4}$ alkyl group as defined anywhere above having a $C_{6-9}$ aryl group as defined anywhere above as a substituent. The $C_{6-8}$ aryl-$C_{2-4}$ alkenyl group may be, for example, and without limitation, a $C_{2-4}$ alkenyl as defined anywhere above having a $C_{6-8}$ aryl group as defined anywhere above as a substituent. The $C_{6-8}$ aryl-$C_{2-4}$ alkynyl group may be, for example, and without limitation, a $C_{2-4}$ alkynyl group as defined anywhere above having a $C_{6-8}$ aryl group as defined anywhere above as a substituent. Non-limiting examples of the 4- to 10-membered non-aromatic heterocyclic group containing one or more heteroatoms which are independently nitrogen, sulfur or oxygen may include pyrrolidinyl, pyrrolinyl, piperidinyl, piperazinyl, imidazolinyl, pyrazolidinyl, imidazolydinyl, morpholinyl, tetrahydropyranyl, azetidinyl, oxetanyl, oxathiolanyl, phthalimide and succinimide. Non-limiting examples of the 5- to 10-membered aromatic heterocyclic group containing one or more heteroatoms which are independently nitrogen, sulfur or oxygen may include pyrrolyl, pyridinyl, pyridazinyl, pyrimidinyl, pirazinyl, imidazolyl, thiazolyl and oxazolyl.

The embodiments involving the formulae as described herein include all possible stereochemical alternatives, including those illustrated or described herein.

In some embodiments, the compounds as described herein or acceptable salts thereof above may be used for systemic treatment or prophylaxis of a viral infection. In some embodiments, the compounds as described herein or acceptable salts thereof above may be used in the preparation of a medicament or a composition for systemic treatment or prophylaxis of a viral infection. In some embodiments, methods of systemically treating any of the infections described herein are also provided. Some embodiments, make use of compositions comprising a compound described herein and a pharmaceutically acceptable excipient or carrier. In some embodiments, the viral infection is caused, at least in part, by an influenza virus. Methods of treating any of the indications described herein are also provided. Such methods may include administering a compound as described herein or a composition of a compound as described herein, or an effective amount of a compound as described herein or composition of a compound as described herein to a subject in need thereof.

Compounds as described herein may be in the free form or in the form of a salt thereof. In some embodiments, compounds as described herein may be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid, an inorganic acid, an organic base or an inorganic base, or by anion exchange or cation exchange from other salts. Those skilled in the art will appreciate that preparation of salts may occur in situ during isolation and/or purification of the compounds or preparation of salts may occur by separately reacting an isolated and/or purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association with the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and/or amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, pharmaceutical compositions in accordance with this invention may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents include those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, $20^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. The formulations may be specifically prepared for intranasal delivery. For example, nasal inhalation.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced viral load, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as less severe infection or delayed or no onset, increased life span, increased life expectancy or prevention of the progression of infection. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods.

In general, compounds described herein should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances, however, such as in severe disease conditions, it may be necessary to administer substantial excesses of the compositions. Some compounds described herein may be toxic at some concentrations. Titration studies may be used to determine toxic and non-toxic concentrations. Toxicity may be evaluated by examining a particular compound's or composition's specificity across cell lines. Animal studies may be used to provide an indication if the compound has any effects on other tissues.

Compounds as described herein may be administered to a subject. As used herein, a "subject" may be a human, non-human primate, rat, mouse, cow, horse, pig, sheep, goat, dog, cat, etc. The subject may be suspected of having or at risk for having an infection, such as viral infection, or suspected of having or at risk for having viral infection. In particular, the infection may mediated by a neuraminidase. Diagnostic methods for viral infection, such as influenza and the clinical delineation of viral infection, such as influenza are known to those of ordinary skill in the art.

TABLE 1 Compounds made and tested for neuraminidase modulatory activity.

TABLE 1

2,3-Fluorinated Glycosides

| Compound | Structure | Compound | Structure |
| --- | --- | --- | --- |
| 4 (N3-100ACD) | 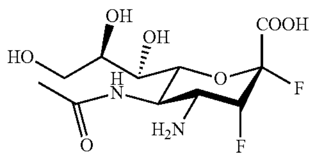 | 7 (N3-102ET) | 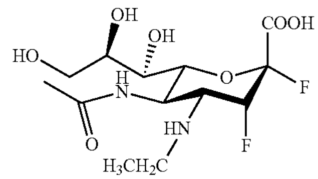 |
| 5 (N3-105ET) | 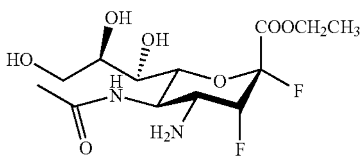 | 9 (N3-111AMD) | 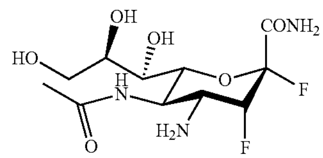 |
| 12 (N3-106GU) | 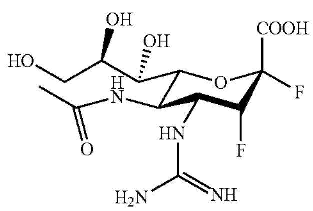 | 8 (N3-109N3) | 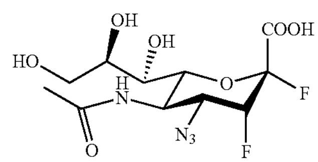 |
| 13 (N3-106ET) | 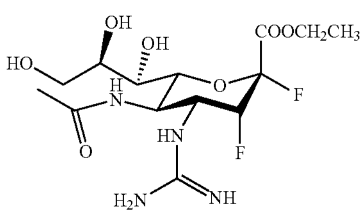 | 11 (N3-107AC) | 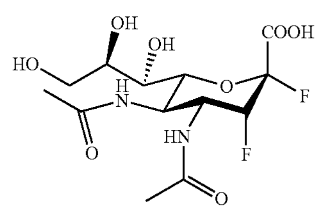 |
| 23DFSA 2,3-Difluorosialic acid | 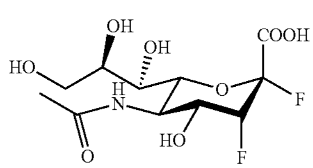 | | |
| C4 Bn | 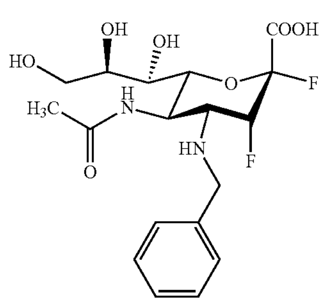 | | |

TABLE 2A Compounds having neuraminidase modulatory activity.

TABLE 2A

| 2,3-Fluorinated Glycosides with Neuraminidase Modulatory Activity | | | |
|---|---|---|---|
| Compound | Structure | Compound | Structure |
| 4 (N3-100ACD) | 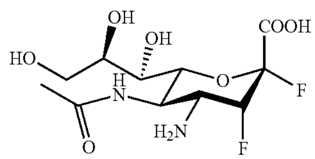  | 7 (N3-102ET) | 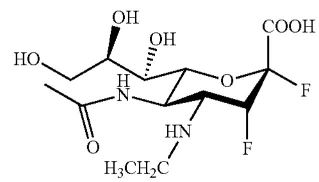  |
| 5 (N3-105ET) | 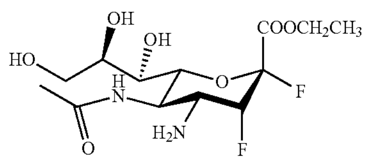  | 9 (N3-111AMD) | 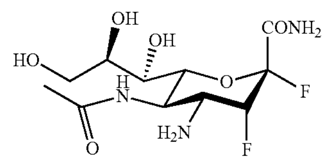  |
| 12 (N3-106GU) | 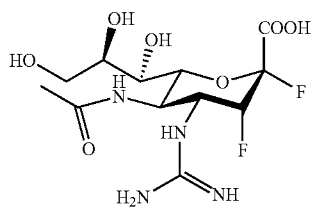  | 13 (N3-106ET) | 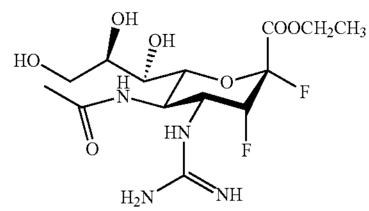  |
| C4 Bn | 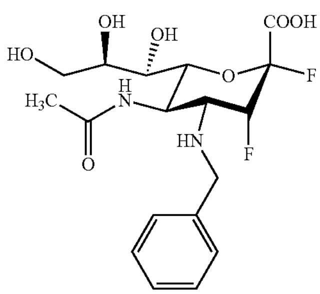  | 8 | 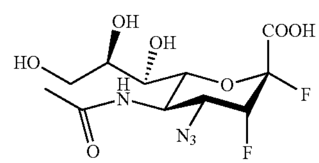  |

TABLE 2B Compounds made and expected to have neuraminidase modulatory activity.

TABLE 2B

| 2,3-Fluorinated Glycosides Compounds |
|---|
|  |
| 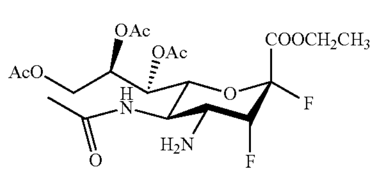  |

TABLE 2B-continued

| 2,3-Fluorinated Glycosides Compounds |
|---|
|  |
|  |

TABLE 2B-continued 2,3-Fluorinated Glycosides Compounds

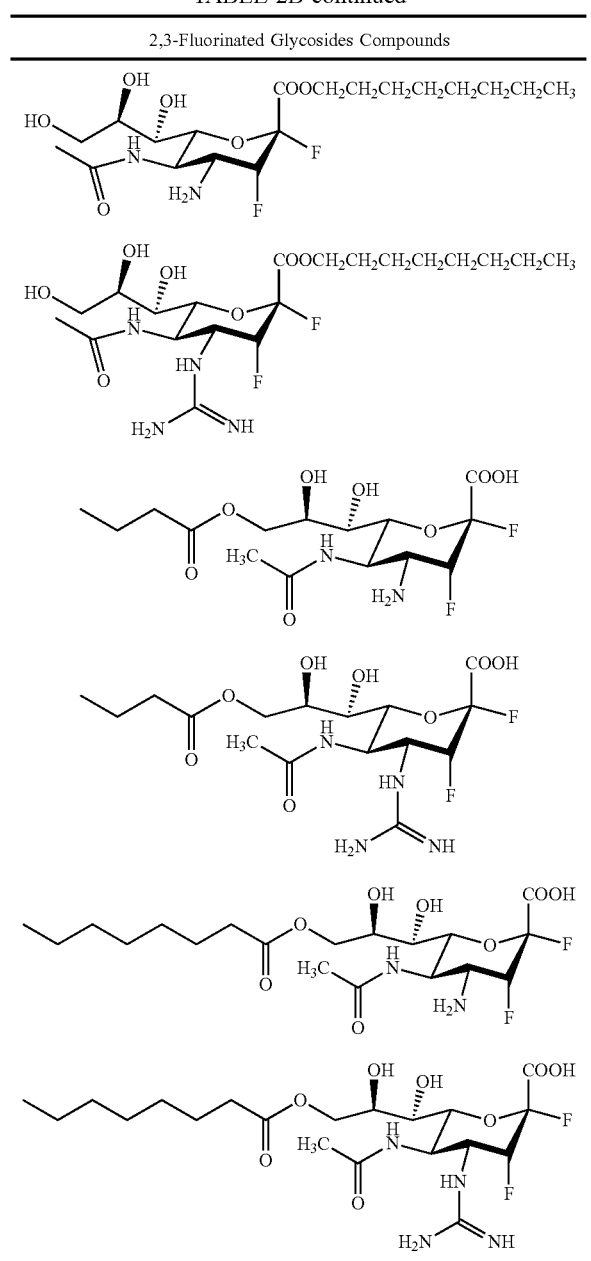

Compounds described herein may also be used in assays and for research purposes.

Compounds for use in the present methods may be synthesized using the methods described herein.

Various alternative embodiments and examples are described herein. These embodiments and examples are illustrative and should not be construed as limiting the scope of the invention.

Previous published work by Hagiwara et al (1994) reported 3-fluoro-sialic acids as being only modest sialidase inhibitors. Specifically, they report two compounds, one with an OH group at carbon 2 (position Z in Formula I). However, the OH group is not a sufficient leaving group to allow trapping of a covalent intermediate. Accordingly, Hagiwara et al. OH compound (at C2 equivalent to Z in Formula I) showed minimal inhibition. Furthermore, the other compound tested by Hagiwara et al., which has a fluorine (a sufficient leaving group) at C2 (equivalent to Z in Formula I), did not have the correct stereochemistry. Accordingly, an appreciation of these requirements was missing in Hagiwara et al.

GENERAL METHODOLOGIES

Synthesis

General methodologies for chemical preparation of compounds of Formula I are described in the following non-limiting exemplary schemes.

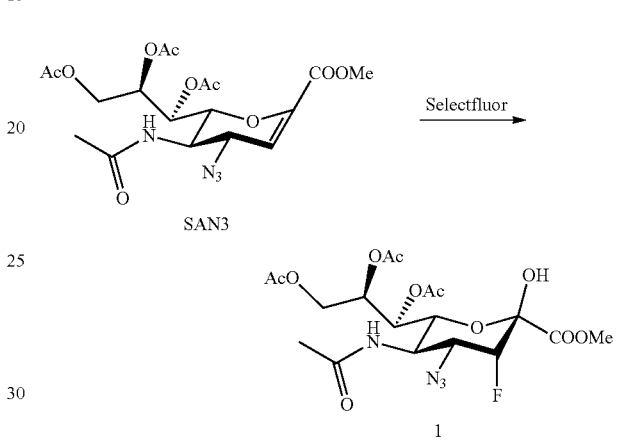

Selectfluor (3.5 eq.) was added to a solution of SAN3 (1 eq.) in $MeNO_2$/water (3/1-4/1) and the solution stirred for 3 days or more to complete the reaction at room temperature (Synthesis of SAN3—Chandler, M. et al. *Journal of the Chemical Society-Perkin Transactions* 1, 1995; 1173-1180). The reaction mixture was quenched with saturated $NaHCO_3$ and extracted with EtOAc. Presence of compound (1) can easily be confirmed via TLC. The axial-F (1) has a lower Rf value than the starting material, and the equitoral-F compound and any other stereoisomers (anomeric hydroxy isomers) would have higher Rf values than the starting material. The fluoride at C3 was detected at −204 ppm on $^{19}F$ NMR experiment, and the stereochemistry was assigned on the basis of $^{1}H$- and $^{19}F$-NMR coupling constants. The coupling constants $J_{H3/F3}$ (47.9 Hz) and $J_{F3/H4}$ (31.0 Hz) are indicative of an axial configuration of the fluorine atoms at C3, respectively.

TABLE 3

Examination for the fluorination at C3 with Selectfluor.

| | condition | Time (Day) | Yields | Selectivity (axial/equitorial) |
|---|---|---|---|---|
| 1 | $MeNO_2$/water (3/1), rt | 3 | 75% | 5/1 |
| 2 | $MeNO_2$/water (3/1), 60° C. | 2 | 62% | 3/1 |
| 3 | DMF/water (8/1), 80° C. | >30 | 40% | 2/1 |
| 4 | MeCN/water (8/1), 60° C. | >30 | 40% | 2/1 |

The reaction can be monitored for completion by UV on TLC, because only the starting material is detected under short UV. The reaction is considered complete upon disappearance of the UV active compound.

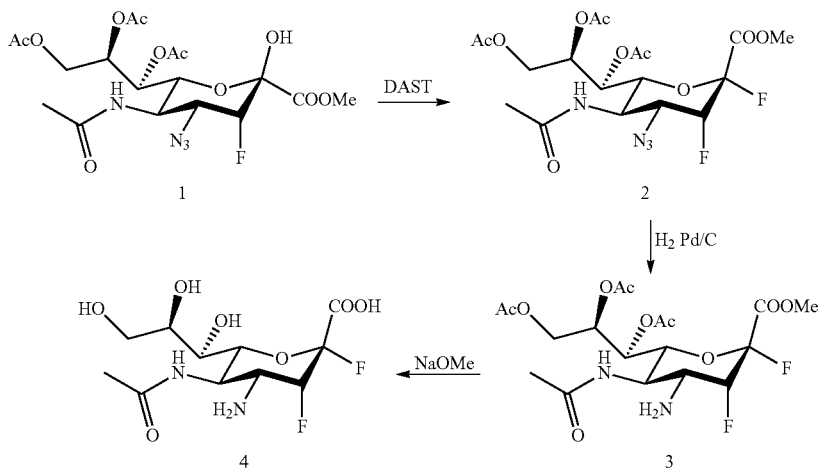

DAST (1.1 eq.) was added drop wise to a suspended solution of compound 1 (1 eq.) in DCM −40° C. and the solution stirred vigorously for 30 min. After the mixture turned clear, the reaction mixture was quenched with saturated NaHCO$_3$ and extracted with DCM and EtOAc to give compound 2. If the reaction mixture doesn't turn clear after 20 min, the reaction mix is placed in a −10° C. bath for the last 10 min.

Compound 2 was hydrogenated with Pd/C in MeOH overnight at room temperature, the catalyst was then filtered off and 6M NaOMe was added to the reaction mixture. The mixture was then acidified with IR120 (H+, strong) to remove the Na+. The resin was filtered off and the filtrate was evaporated and chromatographed (EtOAc/MeOH/water=15/2/1). The hydrogenation was monitored by staining with ninhydrine solution. Both compounds 3 and 4 were isolated.

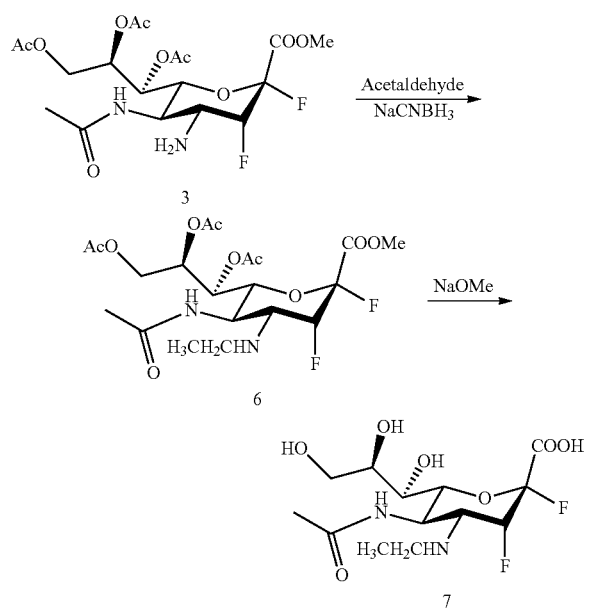

To a solution of compound 3 in MeCN/water (5/1) was added acetaldehyde (2 eq) at room temperature. After 30 min, 4 eq. NaCNBH$_3$ was added and the reaction mixture stirred for 10 min at the same temp. The reaction mixture was quenched with 5% citric acid and chromatographed with EtOAc/acetone (9/1).

The monoacetylated amine (6) was deprotected with 6M NaOMe in wet MeOH to give compound 7.

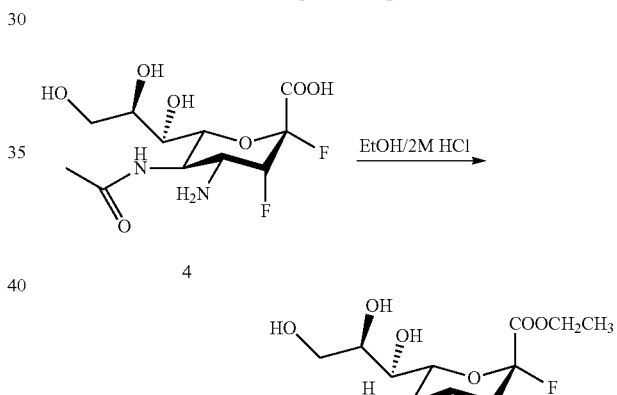

Compound 4 was re-esterified with catalysis HCl (2M HCl in Et$_2$O) in dry EtOH at room temperature. The reaction mixture was left over night and then evaporated. 2 eq. HCl was usually added. The ethyl ester can be separated by silica gel chromatography.

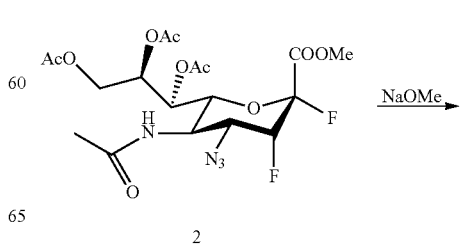

-continued

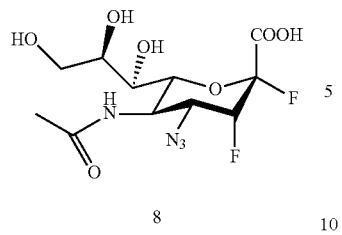

8

The difluorinated compound 2 was deprotected with 6 M NaOMe in wet MeOH at room temperature, and compound 8 was easily purified by silica gel chromatography as 90% yields after acidification with IR120 (strong H+).

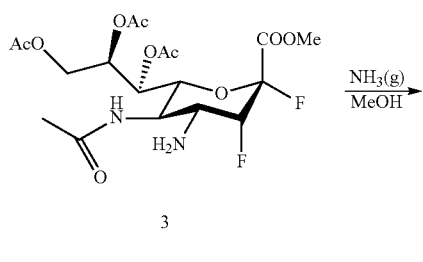

3

$\xrightarrow{\text{NH}_3(g)}{\text{MeOH}}$

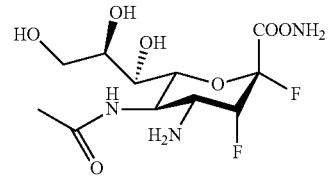

9

The azide 2 was hydrogenated with Pd/C to give compound 3, then $NH_3(g)$ was bubbled to remove acetate and to give amide 4 with good yield.

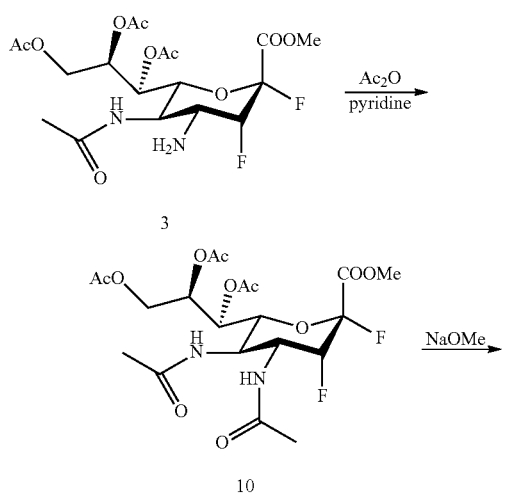

-continued

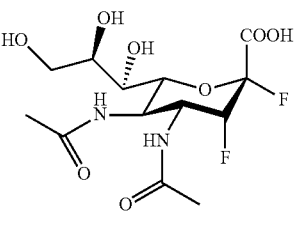

11

For the preparation of compound 11, the amine 3 was acetylated with $Ac_2O$ in pyridine, and O-acetylates and methyl ester were selectively removed with NaOMe. N-acetylated compound 11 was purified and obtained in 70% yield (three steps overall).

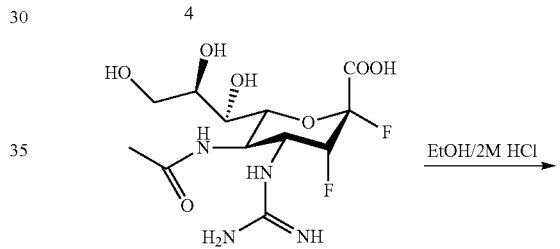

4

$\xrightarrow{\text{3,5-dimethyl pyrazole-1-carboxamide nitrate}}{\text{MeOH}}$

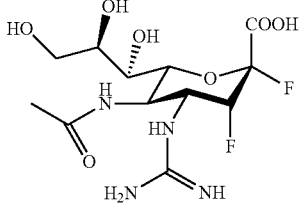

12

$\xrightarrow{\text{EtOH/2M HCl}}$

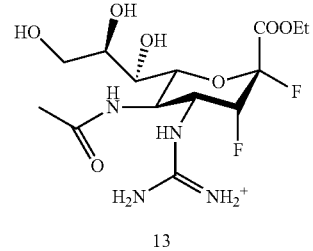

13

The guanylated compound 12 was prepared with 3,5-dimethylpyrazole-1-carboxamidine and $Et_3N$ in MeOH at 60° C. for 3 weeks. The reaction mixture was quenched after three weeks, and 50% of the starting material 4 was successfully recovered. The 4-guanylated 12 was isolated as 80% yield, and the ethylester 13 was given as 80% yield after re-esterification with catalytic HCl in EtOH at room temp for 5 hours.

Compounds of Formula I may be prepared by the chemical methodologies described in the following non-limiting exemplary scheme.

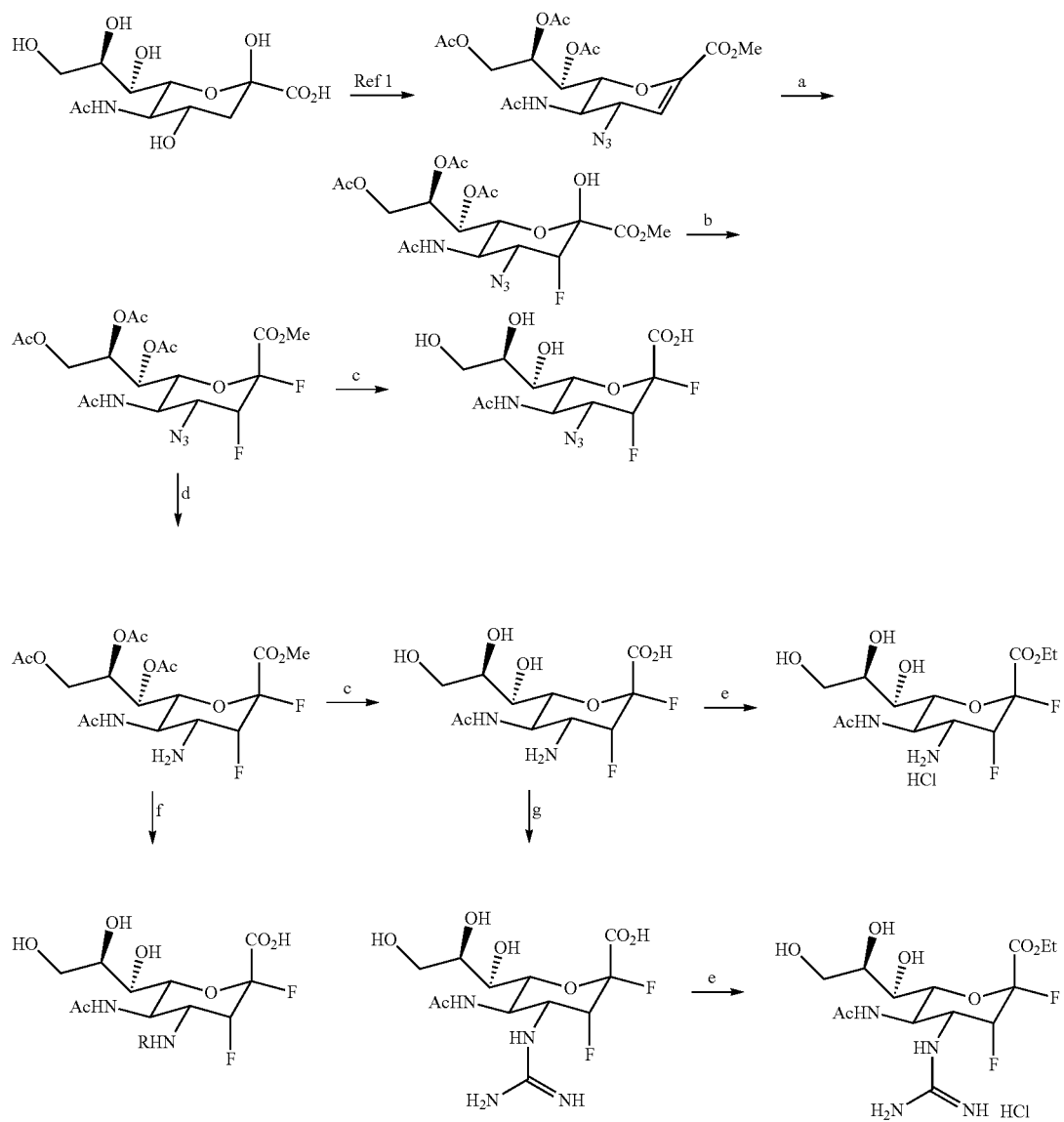

Synthesis of 4-amino derivatives of 2,3-difluorosialic acid. Reagents and conditions are as follows: Ref 1 is Chandler et al. (1995) J Chem Soc. Perk. Trans 1, 1173-1180; (a) 4 eq. Selectfluor, MeNO₂/water (3/1), rt.; (b) DAST, DCM, −40° C. (c) NaOMe, wet MeOH, rt.; (d) Pd/C, H₂, MeOH, rt.; (e) EtOH, cat. HCl, rt.; (f) Acetaldehyde for 4, Benzaldehyde for 5, NaCNBH₃, acetone, rt. and (g) 3,5-dimethylpyrazole-1-carboxamidine nitrate, MeOH, 60° C.

Compounds of Formula I having an amine at C4, may alternatively be prepared by the chemical methodologies described in the following non-limiting exemplary scheme.

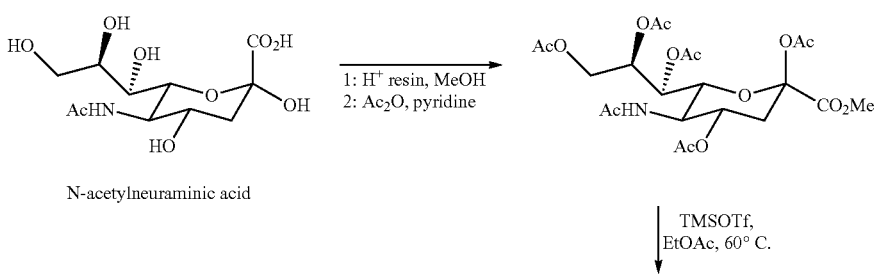

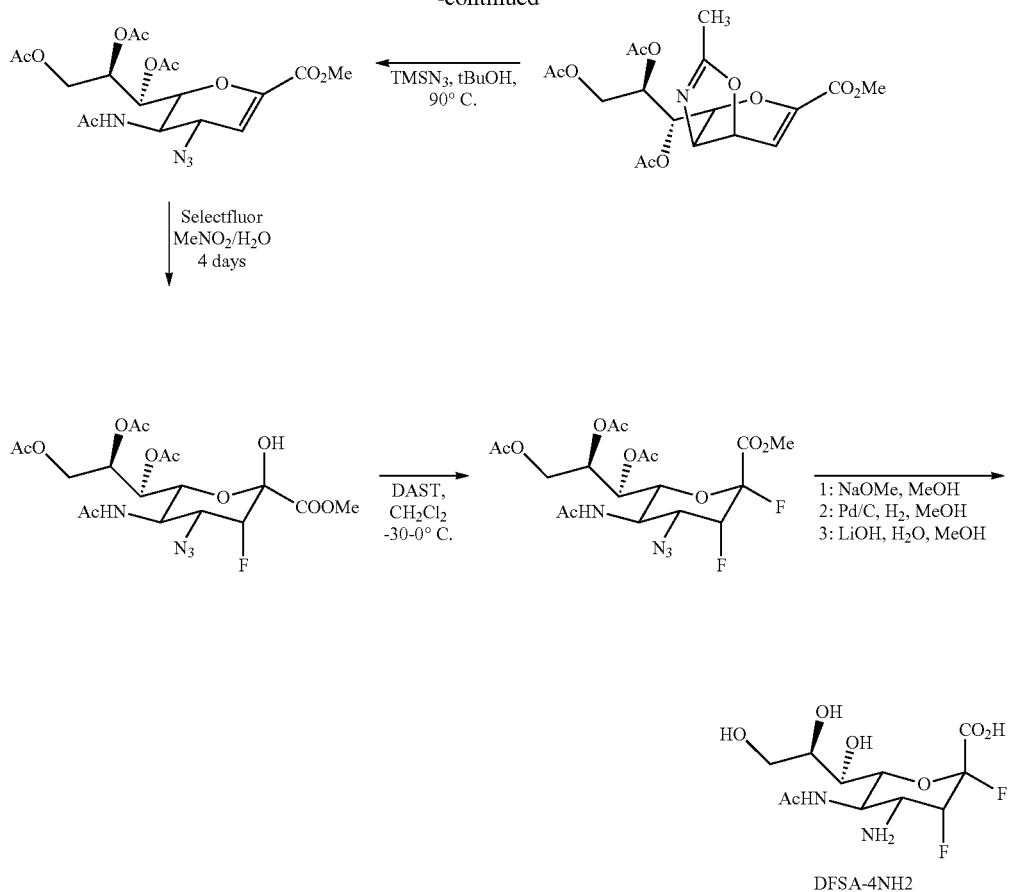
Alternatively, compounds of Formula I having a guanidine at C4, may be prepared by the chemical methodologies described in the following non-limiting exemplary scheme.
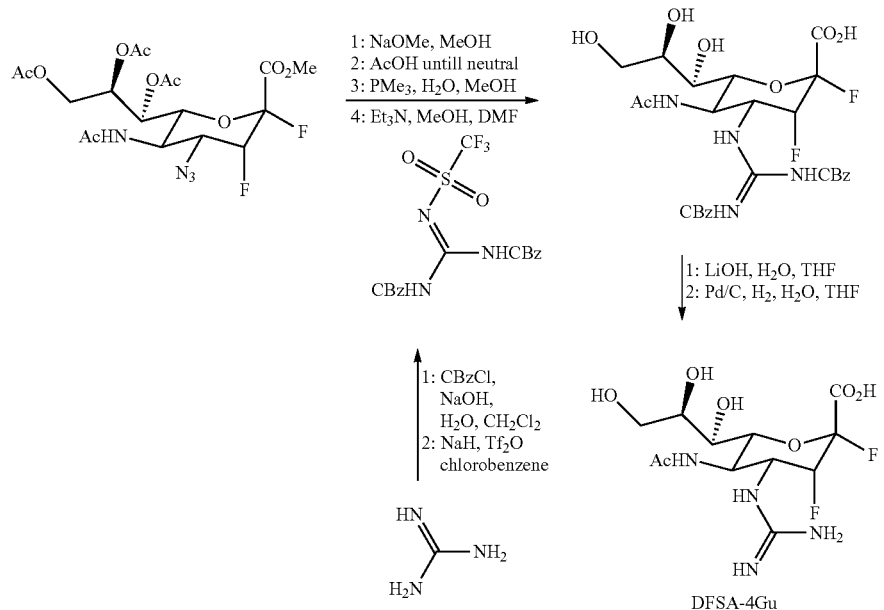

Alternatively, compounds of Formula I may be prepared by the chemical methodologies described in the following non-limiting exemplary scheme.

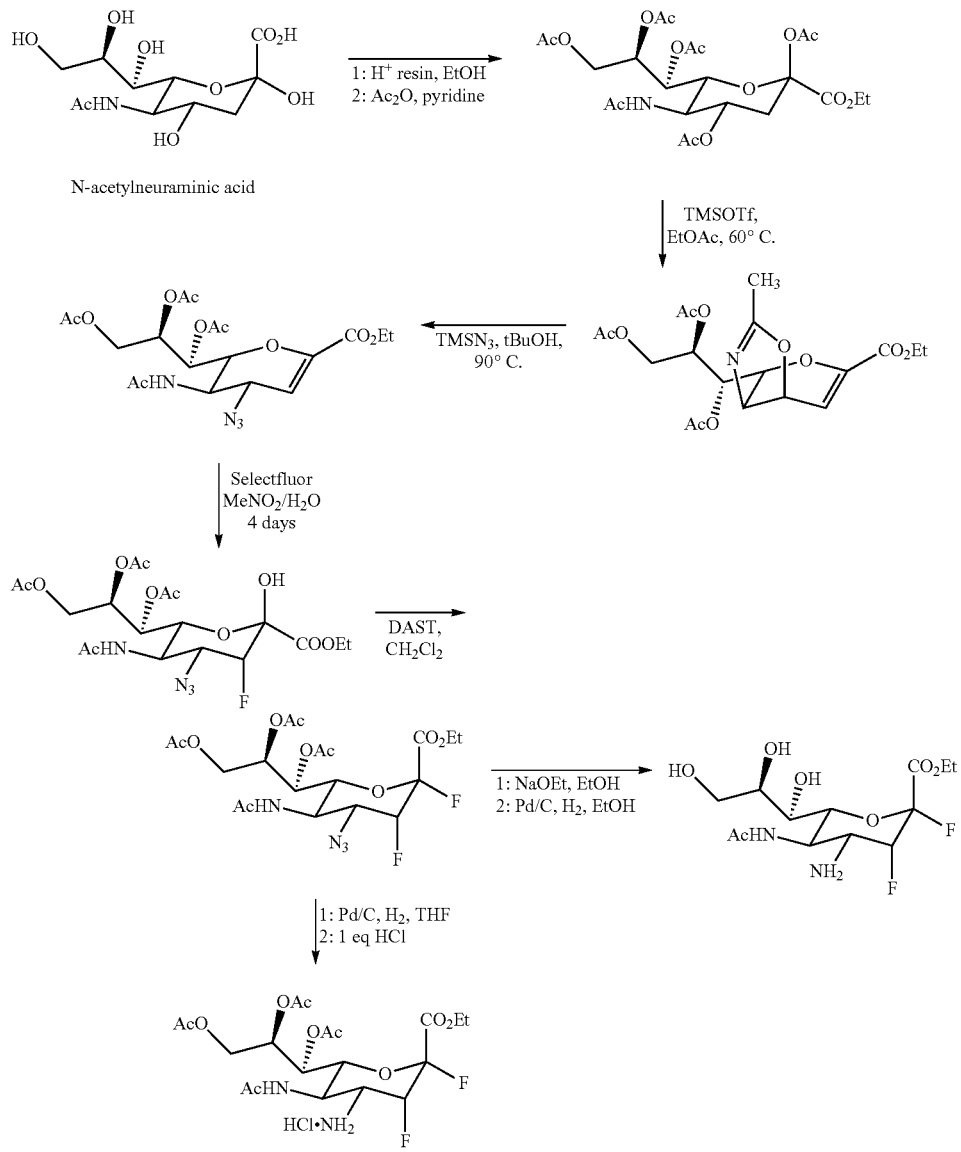

Alternatively, compounds of Formula I having modifications at C1, may be prepared by the chemical methodologies described in the following non-limiting exemplary scheme.

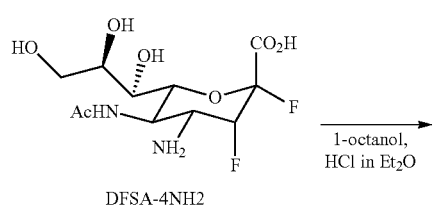

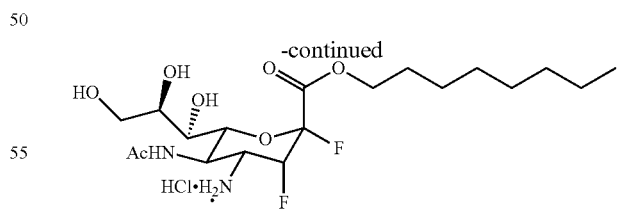

It will be appreciated by a person of skill in the art, that variations in the alkyl chain length may be achieved by substituting 1-octanol (C8—having 8 carbons) for an alternative alcohol. For example, 1-octanol in the above scheme may be substituted for an alternative primary alcohol, which may, for example, be selected from one or more of the following: Propan-1-ol (C3); Butanol (C4); 1-Pentanol (C5); 1-Hexanol (C6); 1-Heptanol (C7); 1-Nonanol (C9); 1-Decanol (C10); Undecanol (C11); Dodecanol (C12); 1-Tetradecanol (C14); Cetyl alcohol (C16); Stearyl alcohol (C18);

and Arachidyl alcohol (C20). Similarly, it will be appreciated that an alternative substrate for this reaction may be chosen. For example, instead of DFSA-4NH2 (compound 4), compound 12 (DFSA-4Gu), or compound 7, etc. may be substituted.

Alternatively, compounds of Formula I having modifications at C1, may be prepared by the chemical methodologies described in the following non-limiting exemplary scheme. For example, a hydrochloric acid salt of ethyl 5-acetamido-4-guanyl-2,3,4,5,-tetradeoxy-3-fluoro-D-erythro-β-L-manno-non-2-ulopyranosylonate fluoride is shown below, which also adds an ethyl group at C1 ($R^1$). It will be appreciated by a person of skill in the art, that variations in the salt produced may be achieved by substituting an alternative acid and that the length of the alkyl group at C1 may be adjusted by substituting an alternative alcohol as set out above.

It will be appreciated by a person of skill in the art, that variations in the alkyl chain length may be achieved by substituting either Trimethyl orthooctyrate (C8—having 8 carbons) or Trimethyl orthobutyrate (C4—having 4 carbons) for an alternative ortho ester derivative. For example, Trimethyl orthooctyrate or Trimethyl orthobutyrate in the above schemes may be substituted for an alternative ortho ester derivative, which may, for example, be selected from one or more of the following: Trimethyl orthoacetate (C2); Trimethyl orthopropionate (C3); Trimethyl orthopentionate (C5); Trimethyl orthohexanate (C6); Trimethyl orthoheptanate (C7); Trimethyl orthononate (C9); Trimethyl orthodecanate (C10). Similarly, it will be appreciated that an alternative substrate for this reaction may be chosen.

Characterization (2R,3R)-4-Azido-4-deoxy-3-fluoro-7,8,9-tri-O-acetyl-sialic acid methyl ester (1)

ESI-MS m/z 515.1 (+Na); $^{19}$F-NMR (CFCl$_3$, 282 MHz) δ −204.7 (dd, J 47.9 and 31.0 Hz); $^1$H NMR (300 MHz) δ 5.32 (1H, m); 5.14 (1H, m); 5.00 (1H, dd, J 31.4 and 1.5 Hz), 4.86 (1H, dd, J 4.5 and 1.9 Hz), 4.25 (1H, m), 4.15 (1H, m), 4.04 (1H, dd, J 12.5 and 8.5 Hz), 3.83 (1H, m), 3.77 (3H, OMe), 2.02 (12H, 4s, 4 Ac)

(2R,3R)-4-Azido-2,4-dideoxy-2,3-difluoro-7,8,9-tri-O-acetyl-sialic acid methyl ester (2)

ESI-MS m/z=517.0 (+Na); $^{19}$F-NMR (CFCl$_3$, 282 MHz) δ −123.2 (1F, t, 8.46 Hz), −217.2 (1F, m); $^1$H-NMR (300 MHz) δ 7.23 (1H, d, NH), 5.97 (1H, m), 5.37 (1H, m), 5.24 (1H, m), 5.10 (1H, dd, J 49.4 and 7.3 Hz), 4.65 (1H, dt, 28.1 and 9.4 Hz), 4.51 (1H, m), 4.27 (2H, m), 3.88 (3H, d, J 7.0 Hz, OMe), 3.39 (1H, m), 2.10 (12H, m, 4 Ac). $^{13}$C NMR (100 MHz) δ 21.6, 21.7, 21.8, 24.5, 49.1, 54.7, 57.8 (dd), 62.7, 68.5, 69.6, 71.6 (d), 78.2, 87.5 (dd), 105.5 (dd), 165.0 (dd), 170.6, 171.4, 172.2, 172.5

(2R,3R)-4-Azido-2,4-dideoxy-2,3-difluorosialic acid (8)

ESI-MS m/z=353.2 (−H); F-NMR (CFCl$_3$, 282 MHz) δ −122.3 (1F, d, J 11.3 Hz), −216.4 (1F, ddd, J 50.1, 29.2 and

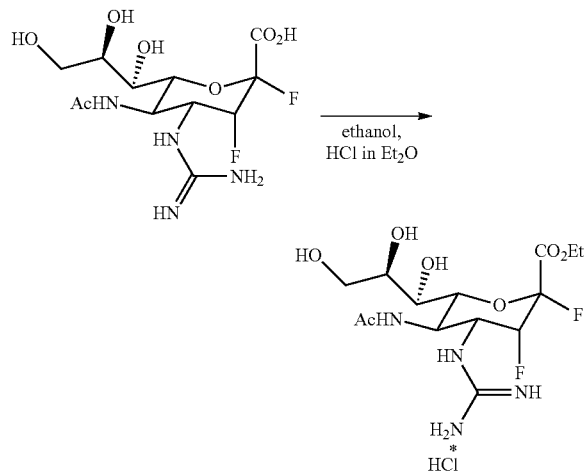

Alternatively, compounds of Formula I having modifications at ring C6, may be prepared by the chemical methodologies described in the following non-limiting exemplary schemes.

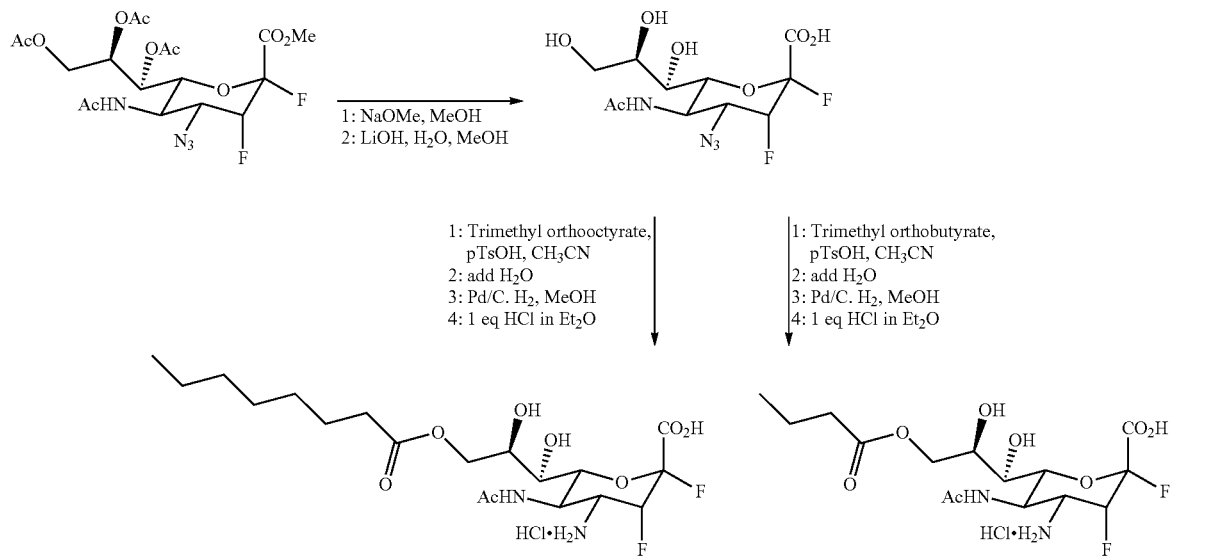

11.3 Hz); $^1$H-NMR (300 MHz) δ 5.30 (1H, dm, J 50.2 Hz), 4.34 (1H, t, J 10.8 Hz), 4.07 (1H, dd, J 29.1 and 11.2 Hz), 3.90 (1H, d, J 10.5 Hz), 3.74 (2H, m), 3.50 (3H, m), 1.95 (3H, s, Ac). $^{13}$C NMR (100 MHz) δ 23.0, 45.9 (d), 61.5 (dd), 63.9, 68.7, 71.1, 74.1 (d), 88.0 (dd), 106.5 (dd), 169.2 (dd), 175.8

(2R,3R)-4-Amino-2,4-dideoxy-2,3-difluorosialylamide (9)

ESI-MS m/z=350.1 (+Na); $^{19}$F-NMR (CFCl$_3$, 282 MHz) δ −121.1 (1F, d, J 8.46 Hz), −219.4 (1F, m); $^1$H-NMR (300 MHz) δ 5.10 (1H, dm, J 49.3 Hz), 4.20 (1H, t, J 10.8 Hz), 3.96 (1H, d J 10.6 Hz), 3.73 (2H, m), 3.50 (3H, m), 1.95 (3H, d, J 1.2 Hz, Ac). $^{13}$C NMR (100 MHz) δ 22.2, 46.1, 51.5 (dd), 63.2, 67.5, 70.1, 74.1, 87.0 (dd) 105.0 (dd), 168.2 (dd), 175.2

(2R,3R)-4-(N-Acetyl) amino-2,4-dideoxy-2,3-difluorosialic acid (11)

ESI-MS m/z=415.1 (+2 Na); $^{19}$F-NMR (CFCl$_3$, 282 MHz) δ −121.8 (1F, d, J 11.9 Hz), −214.4 (1F, m); $^1$H-NMR (300 MHz) δ 5.05 (1H, d, J 50.5 Hz), 4.50 (1H, m), 4.18 (1H, m), 4.05 (1H, d J 10.4 Hz), 3.82 (1H, d, J 10.3 Hz), 3.75 (2H m), 3.48 (2H, m), 1.89 (3H, s, Ac), 1.84 (3H, s, Ac). $^{13}$C NMR (100 MHz) δ 21.6, 21.8 (d), 45.2, 50.8 (m), 63.1, 68.0, 70.5, 70.6, 73.3 (d), 73.5, 169.5 (dd), 174.2, 174.8

(2R,3R)-4-(N-Ethyl) amino-2,4-dideoxy-2,3-difluorosialic acid (7)

ESI-MS m/z=355.3 (−H); $^{19}$F-NMR (CFCl$_3$, 282 MHz) δ −121.8 (1F, d, J 11.5 Hz), −216.4 (1F, m); $^1$H-NMR (300 MHz) δ 5.30 (1H, dm, J 50.2 Hz), 4.29 (1H, t, J 10.7 Hz), 3.82 (1H, d J 10.6 Hz), 3.73 (2H, m), 3.52 (3H, m), 3.00 (2H, m), 1.95 (3H, s, Ac), 1.10 (3H, t, J 7.3 Hz). $^{13}$C NMR (100 MHz) δ 12.4, 23.2, 41.3, 45.2, 58.0 (dd), 63.9, 64.2 (d), 68.7, 71.2, 74.2 (d), 85.5 (dd), 107.2 (dd), 170.0 (dd), 176.1

(2R,3R)-4-Amino-2,4-dideoxy-2,3-difluorosialic acid (4)

ESI-MS m/z=351.2 (+Na); $^{19}$F-NMR (CFCl$_3$, 282 MHz) δ −122.0 (1F, d, J 11.3 Hz), −217.4 (1F, m); $^1$H-NMR (400 MHz) δ 5.10 (1H, ddt, J 50.4, 10.0 and 5.2 Hz), 4.16 (1H, m), 3.73 (3H m), 3.45 (3H, m), 1.91 (3H, dd, J 5.1 and 1.4 Hz, Ac). $^{13}$C NMR (100 MHz) δ 23.1, 46.8, 53.1 (dd), 63.9, 64.1, 68.5, 71.4, 74.4, 89.8 (dd), 108.5 (dd), 170.4 (dd), 176.0

Ethyl (2R,3R)-4-Amino-2,4-dideoxy-2,3-difluorosialylate (5)

ESI-MS m/z=379.1 (+Na); $^{19}$F-NMR (CFCl$_3$, 282 MHz) δ −122.3 (1F, d, J 5.6 Hz), −219.0 (1F, m); $^1$H-NMR (400 MHz) δ 5.10 (1H, ddt, J 49.2, 10.0 and 2.8 Hz), 4.45 (2H, m), 4.14 (1H, m), 4.05 (1H, d J 10.4 Hz), 3.88 (3H m), 3.66 (3H, m), 2.10 (3H, d, J 1.6 Hz, NAc), 1.30 (3H, dt, J 70.4 and 7.2 Hz). $^{13}$C NMR (100 MHz) δ 13.4, 17.1, 22.4, 44.6 (dd), 52.4 (dd), 57.7, 63.2, 65.0, 67.7 (d), 70.1 (d), 73.3 (d), 86.7 (dm), 105.1 (tm), 167.0 (dm), 175.4 (d)

(2R,3R)-4-Guanyl-2,4-dideoxy-2,3-difluorosialic acid (12)

ESI-MS m/z=370.3 (−H); $^{19}$F-NMR (CFCl$_3$, 282 MHz) δ −121.3 (1F, d, J 14.4 Hz), −214.7 (1F, m); $^1$H-NMR (300 MHz) δ 5.00 (1H, dm, J 50.2 Hz), 4.19 (1H, t, J 8.9 Hz), 3.81 (2H, m), 3.52 (3H, m), 3.10 (1H, q, J 7.3 Hz), 1.90 (3H, s, Ac), 1.12 (4H, m). $^{13}$C NMR (100 MHz) δ 22.3, 43.5, 46.5, 55.1, 63.9, 68.9, 71.5, 74.2, 89.5 (dd), 107.0 (dd), 161.5, 170.1 (dd), 175.8,

Ethyl (2R,3R)-4-Guanyl-2,4-dideoxy-2,3-difluorosialylate (13)

ESI-MS m/z=421.4 (+Na); $^{19}$F-NMR (CFCl$_3$, 282 MHz) δ −122.5 (1F, d, J 12.0 Hz), −216.0 (1F, m); $^1$H-NMR (300 MHz) δ 5.16 (1H, dm, J 49.5 Hz), 4.32 (2H, m), 4.18 (2H, m), 4.03 (1H, d, J 9 Hz), 3.70 (2H, m), 3.50 (3H, m), 3.09 (2H, q, J 7.1 Hz), 1.90 (3H, s, Ac), 1.23 (3H, t, J 6.2 Hz).

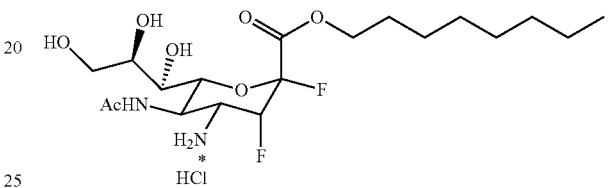

Hydrochloric acid salt of octyl 5-acetamido-4-amino-2,3,4,5,-tetradeoxy-3-fluoro-D-erythro-β-L-manno-non-2-ulopyranosylonate fluoride ESI-MS m/z=463.3 (M+Na); $^1$H-NMR (400 MHz, CH$_3$OD) δ 5.37 (1H, app dt, J 49.92, 5.04), 4.50-4.44 (1H, m), 4.38-4.27 (2H, m), 4.21-4.11 (2H, m), 3.80-3.77 (1H, m), 3.75 (1H, dd, J 6.91, 2.30), 3.69-3.66 (1H, m), 3.60-3.55 (1H, m), 2.04 (3H, s), 1.80-1.73 (2H, m), 1.42-1.28 (10H, m), 0.91 (3H, t, J 7.00).

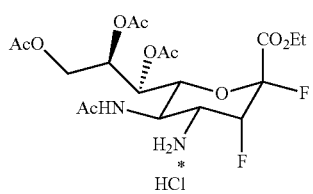 [SMILES: CCOC(=O)C1(F)OC([C@H](OC(C)=O)[C@@H](COC(C)=O)OC(C)=O)C(NC(C)=O)C(N)C1F ; Cl]

Hydrochloric acid salt of ethyl 5-acetamido-7,8,9-tri-O-acetyl-4-amino-2,3,4,5-tetradeoxy-3-fluoro-D-erthro-β-L-manno-non-2-ulopyranosylonate fluoride ESI-MS m/z=483.3 (M+H); $^1$H-NMR (400 MHz, CDCl$_3$) δ 6.99 (1H, s), 5.70-5.23 (3H, m), 5.02 (1H, s), 4.61-4.08 (6H, m), 2.28-1.23 (15H, m).

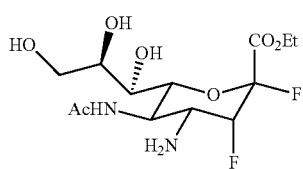 [SMILES: CCOC(=O)C1(F)OC([C@H](O)[C@H](O)CO)C(NC(C)=O)C(N)C1F]

Ethyl 5-acetamido-4-amino-2,3,4,5,-tetradeoxy-3-fluoro-D-erythro-β-L-manno-non-2-ulopyranosylonate fluoride ESI-MS m/z=379.1 (M+Na); $^1$H-NMR (400 MHz, D$_2$O) δ 5.18 (1H, app d, J 49.34), 4.38 (2H, q, J 7.16), 4.20-4.14 (1H, m), 4.01 (1H, d, J 10.51), 3.87-3.76 (2H, m), 3.61 (1H, dd, J 11.95, 5.86), 3.55 (1H, d, J 9.29), 3.39 (1H, dd, J 30.00, 10.96), 2.03 (3H, s), 1.32 (3H, t, J 7.16).

Hydrochloric acid salt of 5-acetamido-4-amino-9-octanoyl-2,3,4,5,-tetradeoxy-3-fluoro-D-erythro-β-L-manno-non-2-ulopyranosylonate fluoride ESI-MS m/z=453.3 (M—H); $^1$H-NMR (400 MHz, MeOD) δ 5.35 (1H, app d, J 45.84), 4.58-4.28 (2H, m), 4.23-3.88 (4H, m), 3.63-3.50 (1H, m), 2.48-2.26 (2H, m), 2.15-1.94 (3H, m), 1.72-1.54 (2H, m), 1.51-1.14 (8H, m), 1.03-0.88 (3H, m).

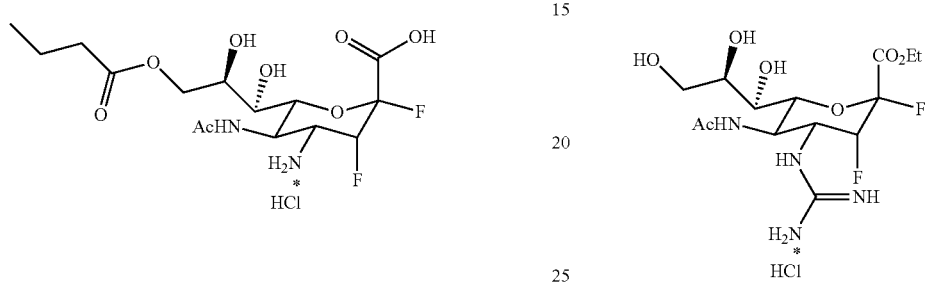

Hydrochloric acid salt of 5-acetamido-4-amino-9-butyroyl-2,3,4,5,-tetradeoxy-3-fluoro-D-erythro-β-L-manno-non-2-ulopyranosylonate fluoride ESI-MS m/z=421.3 (M+Na); $^1$H-NMR (400 MHz, MeOD) δ 5.34 (1H, app d, J 51.62), 4.47 (1H, app t, J 10.66), 4.36 (1H, d, J 10.20), 4.16 (1H, dd, J 11.42, 6.24), 4.09-3.97 (3H, m), 3.55 (1H, d, J 9.14), 2.34 (2H, t, J 7.31), 2.03 (3H, s), 1.70-1.61 (2H, m), 0.96 (3H, t, J 7.31).

Hydrochloric acid salt of ethyl 5-acetamido-4-guanyl-2,3,4,5,-tetradeoxy-3-fluoro-D-erythro-β-L-manno-non-2-ulopyranosylonate fluoride ESI-MS m/z=421.4 (M+Na); $^1$H-NMR (300 MHz, D$_2$O) δ 5.16 (1H, app d, J 49.5 Hz), 4.32 (2H, m), 4.18 (2H, m), 4.03 (1H, d, J 9 Hz), 3.70 (2H, m), 3.50 (3H, m), 3.09 (2H, q, J 7.1 Hz), 1.90 (3H, s), 1.23 (3H, t, J 6.2 Hz).

Synthesis of 3' Equatorial F Compounds

General methodologies for chemical preparation of 3' equatorial compounds of Formula I are described in the following non-limiting exemplary schemes. Furthermore, additional modifications to the below exemplary schemes and alternative syntheses are known in the art.

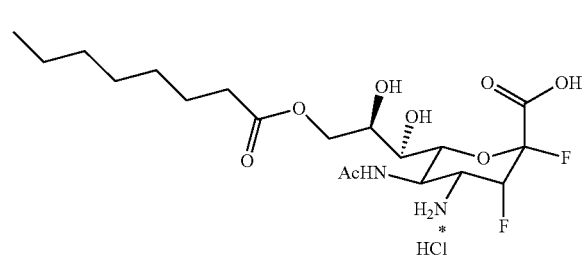 [SMILES: CCCCCCCC(=O)OC[C@@H](O)[C@@H](O)C1OC(F)(C(=O)O)C(F)C(N)C1NC(C)=O ; Cl]

Scheme 1

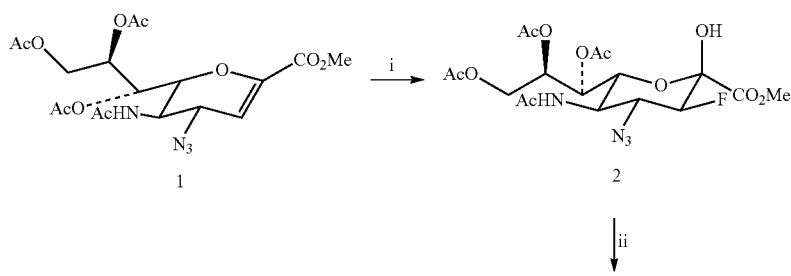

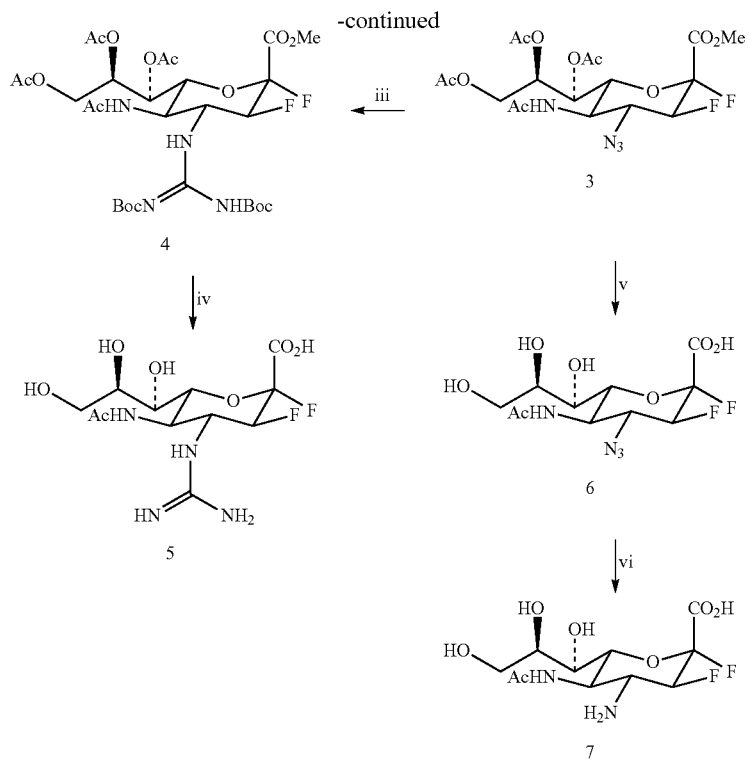

i. CH₃NO₂, H₂O, Selectfluor, rt, 18%. ii. DCM, DAST, −40° C., 91%. iii. EtOAc, Pd/C (10%), DIPEA, N, N'-di-Boc-N''-trifluoromethanesulfonylguanidine, rt, 54%. iv. MeOH, NaOMe; TFA, rt, 70%. v. MeOH, NaOMe; H₂O, rt, 96%. vi. MeOH, Pd/C, rt, 100%.

Compounds of Formula I having modifications at C1, may be prepared by the chemical methodologies described in the following non-limiting exemplary scheme.

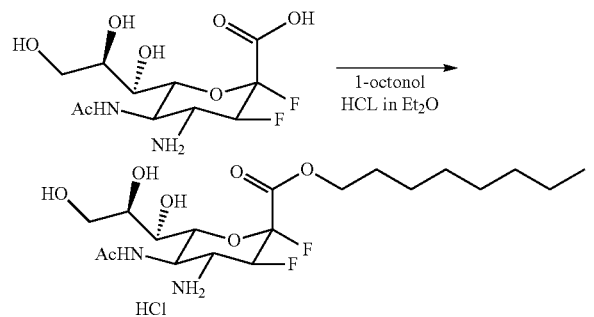

It will be appreciated by a person of skill in the art, that variations in the alkyl chain length may be achieved by substituting 1-octanol (C8—having 8 carbons) for an alternative alcohol. For example, 1-octanol in the above scheme may be substituted for an alternative primary alcohol, which may, for example, be selected from one or more of the following: Propan-1-ol (C3); Butanol (C4); 1-Pentanol (C5); 1-Hexanol (C6); 1-Heptanol (C7); 1-Nonanol (C9); 1-Decanol (C10); Undecanol (C11); Dodecanol (C12); 1-Tetradecanol (C14); Cetyl alcohol (C16); Stearyl alcohol (C18); and Arachidyl alcohol (C20). Similarly, it will be appreciated that an alternative substrate for this reaction may be chosen. For example, instead of the 4NH₂ (compound 7) the 4Gu compound (compound 5), or etc. may be substituted.

Alternatively, compounds of Formula I having modifications at C1, may be prepared by the chemical methodologies described in the following non-limiting exemplary scheme. For example, the below exemplary scheme adds an ethyl group at C1 (R¹). It will be appreciated by a person of skill in the art, that variations in the salt produced may be achieved by substituting an alternative acid and that the length of the alkyl group at C1 may be adjusted by substituting an alternative alcohol as set out above.

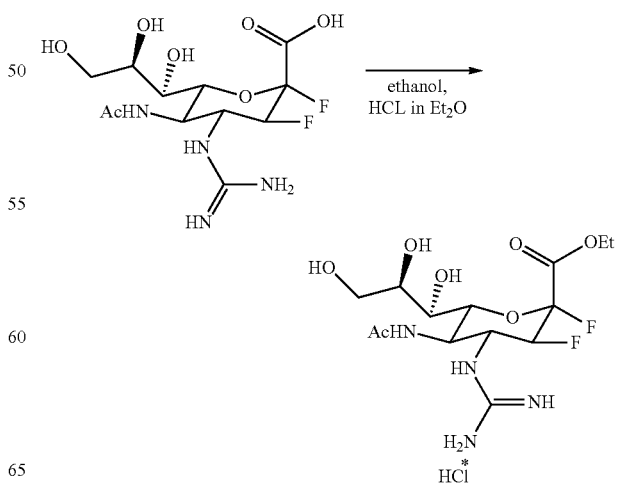

Syntheses and Characterizations of 3' Equatorial F Compounds

Methyl 5-acetamido-7, 8, 9-tri-O-acetyl-4-azido-4, 5-dideoxy-3β-fluoro-D-erythro-L-gluco-nonulo-pyranosonate (2)

A suspension of 1 (11.1 g, 24.3 mmol), nitromethane (95 mL), water (16 mL) and Selectfluor (34.5 g, 97.5 mmol, 4 equiv.) was stirred for 7 days at room temperature. (The reaction may be monitored for completion by UV on TLC, because only the starting material is detected under short UV. The reaction is considered complete upon disappearance of the UV active compound.). The reaction was quenched with saturated NaHCO$_3$ (100 mL), extracted with EtOAc (4×200 mL). The organic phase was washed with saturated NaHCO$_3$ (300 mL) and brine (300 mL), dried over MgSO$_4$. After evaporation, the resulting residue was purified by flash column chromatography (CHCl$_3$/Acetone/EtOAc=5/1/1) to give the desired compound 2 as a white solid (2.14 g, 18%). $^1$H NMR (400 MHz, CDCl$_3$): δ 5.73 (d, 1H, J 9.2 Hz, NHAc), 5.30 (dd, 1H, J$_{7,8}$ 6.7 Hz, H-7), 5.22 (m, 1H, H-8), 4.74 (dd, 1H, J$_{3,4}$ 9.6 Hz, J$_{H3,F3}$ 49.0 Hz, H-3), 4.66 (s, 1H, OH), 4.40 (dd, 1H, J$_{6,7}$ 1.8 Hz, J$_{5,6}$ 10.5 Hz, H-6), 4.37 (dd, 1H, J$_{8,9a}$ 2.1 Hz, H-9a), 4.20 (m, 1H, H-4), 4.04 (dd, 1H, J$_{8,9b}$ 6.3 Hz, J$_{9a,9b}$ 12.4 Hz, H-9b), 3.96 (s, 3H, OCH$_3$), 3.77 (m, 1H, H-5), 2.15 (s, 3H, CH$_3$CO), 2.11 (s, 3H, CH$_3$CO), 2.04 (s, 3H, CH$_3$CO), 2.03 (s, 3H, CH$_3$CO). $^{13}$C NMR (75 MHz, CDCl$_3$): δ 170.9, 170.7, 170.6 (2C), 167.8, 93.3 (d, J$_{C2,F3}$ 21.8 Hz, C-2), 89.2 (d, J$_{C3,F3}$ 193.8 Hz, C-3), 70.5, 69.6, 67.7, 62.6, 62.0 (d, J$_{C4,F3}$ 17.2 Hz, C-4), 54.55, 49.9 (d, J$_{C5,F3}$ 6.0 Hz, C-5), 23.6, 21.2, 21.0, 20.9. $^{19}$F NMR (282 MHz, CDCl$_3$): δ −195.46 (s, F-2 eq). ESI-MS: 515.3 [(M+Na)$^+$].

Methyl 5-acetamido-7, 8, 9-tri-O-acetyl-4-azido-2, 4, 5-trideoxy-2α, 3β-difluoro-α-D-erythro-L-gluco-nonulopyranosonate (3)

To a suspension of 2 (0.62 g, 1.3 mmol) in dry DCM (18 mL) was added dropwise DAST (0.18 mL, 1.4 mmol, 1.1 equiv) with stirring under N$_2$ at −40° C. After addition, the reaction mixture was stirred for 0.5 h at −40° C., and then gradually warmed up to −10° C. The reaction was quenched with saturated NaHCO$_3$, diluted with DCM (50 mL) and washed with brine (30 mL). The water phase was extracted again with EtOAc (2×50 mL) and washed with brine (50 mL). The combined organic phase was dried over MgSO$_4$. After evaporation, the resulting residue was purified by flash column chromatography (DCM/Acetone=8/1) to give product 3 as a white solid (0.566 g, 91%). $^1$H NMR (400 MHz, CDCl$_3$): δ 5.59 (d, 1H, J 9.0 Hz, NHAc), 5.32 (m, 1H, H-8), 5.24 (dt, 1H, J$_{7,8}$ 8.5 Hz, H-7), 4.70 (dd, 1H, J$_{5,6}$ 10.7 Hz, J$_{6,7}$ 1.6 Hz, H-6), 4.66 (ddd, 1H, J$_{4,5}$ 10.7 Hz, J$_{H4,F3}$ 20.2 Hz, H-4), 4.47 (ddd, 1H, J$_{3,4}$ 9.3 Hz, J$_{H3,F3}$ 48.6 Hz, J$_{H3,F2}$ 14.5 Hz, H-3), 4.25 (dd, 1H, J$_{8,9a}$ 2.6 Hz, H-9a), 4.13 (dd, 1H, J$_{8,9b}$ 5.2 Hz, J$_{9a,9b}$ 12.5 Hz, H-9b), 3.91 (s, 3H, OCH$_3$), 3.62 (m, 1H, H-5), 2.14 (s, 3H, CH$_3$CO), 2.08 (s, 3H, CH$_3$CO), 2.05 (s, 3H, CH$_3$CO), 2.04 (s, 3H, CH$_3$CO). $^{13}$C NMR (75 MHz, CDCl$_3$): δ 171.0, 170.7, 170.5, 169.7, 165.3 (d, J$_{C2,F2}$ 32.8 Hz, C-1), 105.5 (dd, J$_{C2,F2}$ 229.1 Hz, J$_{C2,F3}$ 27.2 Hz, C-2), 92.0 (dd, J$_{C3,F3}$ 192.2 Hz, J$_{C3,F2}$ 29.0 Hz, C-3), 72.9, 68.9, 67.0, 62.2, 61.8 (dd, J$_{C4,F3}$ 18.1 Hz, J$_{C4,F2}$ 8.4 Hz, C-4), 53.7, 49.2 (d, J$_{C5,F3}$ 6.9 Hz, C-5), 23.5, 21.0 (2C), 20.9. $^{19}$F NMR (282 MHz, CDCl$_3$): δ −119.4 (d, J$_{F2,F3}$ 12.7 Hz, F-2 eq), −197.5 (d, F-3 eq). ESI-MS: 517.2 [(M+Na)$^+$].

Methyl 5-acetamido-7, 8, 9-tri-O-acetyl-4-[(N',N''-di-tert-butoxycarbonyl) guanidine]-2, 4, 5-trideoxy-2α, 3β-difluoro-α-D-erythro-L-gluco-nonulpyranosonate (4)

A mixture of 3 (260 mg, 0.53 mmol), EtOAc (10 mL), Pd/C (10%, 60 mg), N, N'-di-Boc-N''-trifluoromethanesulfonylguanidine (350 mg, 0.9 mmol, 1.7 equiv) and DIPEA (0.2 mL) was placed under vacuum and then filled with hydrogen three times, and the mixture was stirred under a H$_2$ atmosphere for 24 h at room temperature. The reaction mixture was filtered through a short pad of Celite and washed with EtOAc. After evaporation, the resulting residue was purified by flash column chromatography (DCM/Acetone=15/1) to give the product 4 as a white solid (0.311 g, 83%). $^1$H NMR (400 MHz, CDCl$_3$): δ 11.37 (s, 1H, NHBoc), 8.67 (d, 1H, J 7.8 Hz, NHGuanidine), 6.45 (d, 1H, J 9.0 Hz, NHAc), 5.32 (m, 1H, H-8), 5.25 (brd, 1H, J$_{7,8}$ 7.7 Hz, H-7), 4.90 (m, 1H, H-4), 4.71 (ddd, 1H, J$_{3,4}$ 8.8 Hz, J$_{H3,F3}$ 48.5 Hz, J$_{H3,F2}$ 12.5 Hz, H-3), 4.50 (brd, 1H, H-6), 4.32 (dd, 1H, J$_{8,9a}$ 2.6 Hz, H-9a), 4.28 (m, 1H, H-5), 4.07 (dd, 1H, J$_{8,9b}$ 6.2 Hz, J$_{9a,9b}$ 12.4 Hz, H-9b), 3.90 (s, 3H, OCH$_3$), 2.15 (s, 3H, CH$_3$CO), 2.09 (s, 3H, CH$_3$CO), 2.04 (s, 3H, CH$_3$CO), 1.88 (s, 3H, CH$_3$CO), 0.99 (s, 18H, 2× Boc). $^{13}$C NMR (75 MHz, CDCl$_3$): δ 171.2, 171.1, 170.2, 169.8, 165.1 (d, J$_{C2,F2}$ 32.8 Hz, C-1), 162.7, 157.5, 152.9, 105.7 (dd, J$_{C2,F2}$ 226.7 Hz, J$_{C2,F3}$ 27.8 Hz, C-2), 90.4 (dd, J$_{C3,F3}$ 191.8 Hz, J$_{C3,F2}$ 31.9 Hz, C-3), 84.4, 80.3, 74.7, 69.3, 67.2, 62.5, 53.7, 52.8 (dd, J$_{C4,F3}$ 20.3 Hz, J$_{C4,F2}$ 6.2 Hz, C-4), 49.0 (d, J$_{C5,F3}$ 5.0 Hz, C-5), 28.3 (3C), 28.1 93C), 23.1, 21.0 (2C), 20.9. $^{19}$F NMR (282 MHz, CDCl$_3$): δ −115.6 (d, J$_{F2,F3}$ 11.3 Hz, F-2 eq), −195.8 (d, F-3 eq). ESI-MS: 733.4 [(M+Na)$^+$].

5-Acetamido-2, 4, 5-trideoxy-2α, 3β-difluoro-4-guanidino-α-D-erythro-L-gluco-nonulopyranosonate (5)

To a solution of 4 (71 mg, 0.1 mmol) in dry methanol (6 mL) was added sodium methylate solution (5.4 M, 0.1 mL) under N$_2$, and the reaction mixture was stirred overnight at room temperature. The reaction was neutralized with Amberlite (IR-120), filtered and washed with methanol, evaporated to give a residue. The resulting residue was dissolved into TFA (1 mL) and stirred for 2 h at room temperature, evaporated and co-evaporated with toluene three times. The crude product was purified by flash column chromatography (EtOAc/MeOH/H$_2$O=7/2/1) to give compound 5 as a white solid (26 mg, 92%). $^1$H NMR (400 MHz, D$_2$O): δ 4.71 (ddd, 1H, J$_{3,4}$ 8.9 Hz, J$_{H3,F3}$ 48.8 Hz, J$_{H3,F2}$ 13.4 Hz, H-3), 4.56 (ddd, 1H, J$_{H4,F3}$ 19.0 Hz, H-4), 4.49 (brd, 1H, H-6), 4.36 (t, 1H, J$_{4,5}$=J$_{5,6}$ 10.5 Hz, H-5), 3.84 (dd, 1H, J$_{8,9a}$ 2.6 Hz, H-9a), 3.79 (m, 1H, H-8), 3.62 (dd, 1H, J$_{8,9b}$ 6.0 Hz, J$_{9a,9b}$ 11.5 Hz, H-9b), 3.56 (brd, 1H, J$_{7,8}$ 9.1 Hz, H-7). $^{13}$C NMR (75 MHz, D$_2$O): δ 174.6, 169.6 (d, J$_{C2,F2}$ 30.8 Hz, C-1), 157.6, 106.8 (dd, J$_{C2,F2}$ 222.1 Hz, J$_{C2,F3}$ 27.8 Hz, C-2), 91.5 (dd, J$_{C3,F3}$ 188.1 Hz, J$_{C3,F2}$ 31.5 Hz, C-3), 73.5, 69.9, 67.9, 63.2, 55.7 (dd, J$_{C4,F3}$ 18.8 Hz, J$_{C4,F2}$ 8.2 Hz, C-4), 48.4 (d, J$_{C5,F3}$ 6.4 Hz, C-5), 21.9. $^{19}$F NMR (282 MHz, D$_2$O): δ −112.7 (d, J$_{F2,F3}$ 12.7 Hz, F-2 eq), −199.2 (d, F-3 eq). ESI-MS: 369.4 [(M−H)$^-$].

5-Acetamido-2, 4, 5-trideoxy-4-azido-2α, 3β-difluoro-α-D-erythro-L-gluco-nonulo-pyranosonate (6)

To a solution of 3 (50 mg, 0.1 mmol) in dry methanol (5 mL) was added sodium methylate solution (5.4 M, 50 μL) under N$_2$, and the reaction mixture was stirred for 2 h at room temperature. To the reaction mixture was added a couple drops of water, and stirred for another an hour at room temperature. The reaction was neutralized with Amberlite (IR-120), filtered and washed with methanol, and evaporated to give a residue. The resulting residue was purified by flash column chromatography (EtOAc/MeOH/H$_2$O=12/2/1) to give product 6 as a white solid (34 mg, 96%). $^1$H NMR (400 MHz, CD$_3$OD): δ 4.69 (ddd, 1H, J$_{H4,F3}$ 19.7 Hz, H-4), 4.43 (ddd, 1H, J$_{3,4}$ 9.0 Hz, J$_{H3,F3}$ 50.0 Hz, J$_{H3,F2}$ 13.5 Hz, H-3), 4.39 (brd, 1H, H-6), 4.11 (t, 1H, J$_{4,5}$=J$_{5,6}$ 10.6 Hz, H-5), 3.79 (dd, 1H, J$_{8,9a}$ 2.8 Hz, H-9a), 3.77 (m, 1H, H-8), 3.64 (dd, 1H, J$_{8,9b}$ 5.2 Hz, J$_{9a,9b}$ 11.3 Hz, H-9b), 3.49 (brd, 1H, J$_{7,8}$ 9.1 Hz, H-7). $^{13}$C NMR (75 MHz, CD$_3$OD): δ 173.2, 169.0 (d, J$_{C2,F2}$ 45.4 Hz, C-1), 106.5 (dd, J$_{C2,F2}$ 222.6 Hz, J$_{C2,F3}$ 28.0 Hz, C-2), 92.6 (dd, J$_{C3,F3}$ 188.8 Hz, J$_{C3,F2}$ 30.3 Hz, C-3), 73.9, 70.4, 68.4, 63.4, 63.1 (dd, J$_{C4,F3}$ 24.8 Hz, J$_{C4,F2}$ 8.0 Hz, C-4), 49.1 (d, J$_{C5,F3}$ 6.3 Hz, C-5), 21.4. $^{19}$F NMR (282 MHz, CD$_3$OD): δ −115.7 (d, J$_{F2,F3}$ 11.3 Hz, F-2 eq), −199.6 (d, F-3 eq). ESI-MS: 353.2 [(M−H)$^−$].

5-Acetamido-2, 4, 5-trideoxy-4-amino-2α, 3β-difluoro-α-D-erythro-L-gluco-nonulo-pyranosonate (7)

A suspension of 6 (39 mg, 0.11 mmol) and Pd/C (10%, 12 mg) in dry methanol (8 mL) was vacuumed and filled with hydrogen for three times, and stirred overnight under H$_2$ atmosphere at room temperature. The reaction mixture was filtered through a short pad of Celite and washed with methanol. The organic solvent was evaporated to give a solid. The solid was dissolved in distilled water and filtered with MILLEX-GP filter unit (pore size: 0.22 m), and then lyophilized to give compound 7 as a white solid (36 mg, 100%). $^1$H NMR (400 MHz, D$_2$O): δ 4.83 (ddd, 1H, J$_{3,4}$ 9.1 Hz, J$_{H3,F3}$ 49.6 Hz, J$_{H3,F2}$ 13.2 Hz, H-3), 4.46~4.28 (m, 3H, H-4, H-5 & H-6), 3.84 (dd, 1H, J$_{8,9a}$ 2.5 Hz, H-9a), 3.79 (m, 1H, H-8), 3.62 (dd, 1H, J$_{8,9b}$ 6.0 Hz, J$_{9a,9b}$ 11.7 Hz, H-9b), 3.54 (brd, 1H, J$_{7,8}$ 9.0 Hz, H-7). $^{13}$C NMR (100 MHz, D$_2$O): δ 175.1, 169.2 (d, J$_{C2,F2}$ 30.0 Hz, C-1), 106.4 (dd, J$_{C2,F2}$ 222.0 Hz, J$_{C2,F3}$ 28.0 Hz, C-2), 90.1 (dd, J$_{C3,F3}$ 186.0 Hz, J$_{C3,F2}$ 33.0 Hz, C-3), 73.6, 69.9, 67.7, 63.2, 54.0 (dd, J$_{C4,F3}$ 18.0 Hz, J$_{C4,F2}$ 7.0 Hz, C-4), 46.9 (d, J$_{C5,F3}$ 6.0 Hz, C-5), 22.2. $^{19}$F NMR (282 MHz, D$_2$O): δ −113.6 (d, J$_{F2,F3}$ 14.1 Hz, F-2 eq), −199.9 (d, F-3 eq). ESI-MS: 327.3 [(M−H)$^−$].

Enzyme Kinetics

All experiments were carried out in 20 mM Tris/50 mM CaCl$_2$ buffer, pH 7.6 containing 0.1% BSA. Cuvettes had a path length of 1 cm and were used in either Cary 4000 or Cary 300 UV/visible spectrophotometer connected to a circulating water bath. The data were analyzed using the program GraFit 4.0 (Erithacus software). Time-dependent inactivations were performed by pre-incubating the enzyme at 30° C. in the presence of several concentrations of inactivator. Residual enzyme activity was determined at appropriate time intervals by the addition of an aliquot of the inactivation mixture to an assay solution containing 0.5 mM 4-trifluoromethylumbelliferyl sialic acid (CF3MUSA). Kinetic parameters were determined by measuring the initial linear increase in absorbance at 385 nm. The initial rates at each time point were plotted as a function of time to obtain time-dependent exponential decay curves from which k$_{i\ obs}$ could be obtained for each inactivator concentration using the equation:

$$(\text{rate})_t = (\text{rate})_{t=0} e^{(k_{i\ obs}\ t)} + \text{offset}.$$

The offset was used because the rates did not decay to zero. The inactivation rate constant (k$_i$) and the reversible dissociation constant for the inactivator (K$_d$) were determined by plotting k$_{i\ obs}$ versus inactivator concentration to the equation:

$$k_{i\ obs} = k_i[I]/(K_d + [I]).$$

In the case [I]<<K$_d$, a second-order rate constant (k$_i$/K$_d$) was determined by fitting the data to the equation:

$$k_{i\ obs} = k_i[I]/K_d.$$

Time-dependent reactivations were performed by applying the inactivated enzyme solution (50 µl) to Amicon™ 10 K filter (Millipore™) to remove excess inactivator. The filter was washed 5-times with 150 µL buffer at 4° C. Enzyme activity was assayed at time intervals by the addition of an aliquot of eluted enzyme to an assay solution containing 0.5 mM CF3MUSA. First-order rate constants for reactivation at each acceptor concentration (k$_{r\ obs}$) were determined by direct fit of the activity versus time data to a first-order equation. Reactivation experiments were attempted but no significant enzyme activity could be detected over time, suggesting that the hydrolysis of the sialyl-enzyme intermediate is very slow. The Ki was determined by fitting the data to the equation:

$$K_i = K_d(k_{hyd}/k_i).$$

Cell-Based Assay of Influenza Anti-Viral Activity

Compounds were tested for antiviral activity using a cell based assay, which consists of making serial 2-fold dilutions of the antiviral compounds (from 1:2 to 1:4096 in MegaVir medium in enough volume for the number of viruses tested—60 uL per virus), to which is added 100 infectious units of the specific influenza virus and the preparations are transferred to monolayers of MDCK cells in a microtitre plate. The assay was carried out on a 96-well microtitre plate. The plate is monitored for the development of influenza cytopathic effects from days 3 to 5 post infection. Antiviral activity is determined by the inhibition of development of cytopathic effects. The highest dilution of the compound at which the monolayers are intact is taken as the end-point. Zanamivir was used as a positive control.

Dilution Preparations:
1. In row A on a clean 96-well microtitre plate, prepare 2-fold serial dilutions of antiviral compounds from 1:2 to 1:4096 in MegaVir medium in enough volume for the number of viruses tested (60 uL per virus).
2. Transfer 55 uL of the 2-fold dilution series to a clean row in the 96-well microtitre plate.
3. To the 55 uL dilution series, add 55 uL of diluted influenza virus (at 100 TCID$_{50}$ per 25 ul). Also add virus to positive control wells.
4. To the now 110 uL mixture, add 55 uL of 4×TPCK-treated trypsin. Add trypsin also to positive and negative control wells. Mix well.
5. Prepare also 2-fold serial dilutions from 1:2 to 1:256 for the inoculating virus in MegaVir medium for back titration.

Plate Inoculation:
6. In a 96-well microtitre plate containing confluent monolayers of MDCK cells in ~200 uL MegaVir medium, transfer 75 uL of the mixture to 2 respective rows as duplicates.
7. Transfer 50 uL of the positive control, and 25 uL of negative controls to respective wells.
8. Transfer also 25 uL of the virus back titration in duplicates.

9. Therefore in each well:
    a. Samples: 25 uL compounds+25 uL virus+25 uL trypsin
    b. Positive control: 25 uL virus+25 uL trypsin (no compounds)
    c. Negative control: 25 uL trypsin (no compounds or virus)
    d. Back titration: 25 uL virus
10. The plates are incubated at 37 C in a $CO_2$ incubator for 3 days, then observed for the appearance of cytopathic effects on day 3 and day 5.

In Vivo Pharmacokinetic (PK) Profile Study

Dose Administration

Intravenous (IV) injections—Mice were injected with the required volume to administer the prescribed dose (mg/kg) to the animals based on individual mouse weight using a 28 G needle. The injection volume was 200 µL/20 g mouse. The mice were briefly restrained during IV injections for approx. 1 minute. Dilation of the vein was achieved by holding the animals under a heating lamp for a period of between 1-2 minutes.

Intra-nasal (IN) administration—Mice were anesthetized with isoflurane 2% and 2 L/O2/min until the absence of a toe pinch reflex. Animals were restrained in an upright position and using a micropipette, animals were instilled with 10 µL of the compounds into each nostril per 15 g of body weight. The mice were briefly restrained during the instillation procedure for approx. 20 seconds and the rate of release was adjusted to allow the mice to inhale the compounds without forming bubbles. The mouse was placed back in the anesthetic chamber in an inverted position for an additional 2 minutes or until breathing returned to normal.

Pharmacokinetic Sampling

Mice were individually weighed and evenly distributed into groups according to weight. Mice (n=20/group and n=4/time point) were injected with the test articles as described in the dose administration section.

Blood collection: Blood was collected at the time points indicated in the study grouping table. For blood collection, mice were terminated by $CO_2$ inhalation and blood was collected by cardiac puncture. Upon last breath, mice were removed from inhalation chamber and approx 500-700 µL of blood was collected by cardiac puncture with a 25 G needle and placed into the appropriate EDTA microtainer tube. Each tube was inverted several times to ensure even mixing of blood and EDTA to prevent coagulation. Blood samples were stored on ice until all samples were collected for a particular time point and will then further processed to generate plasma.

Plasma preparation: Plasma was prepared by centrifuging samples at 2500 rpm for 15 minutes at 4° C. (rpm based on Beckman GH 3.8A rotor, $RCF_{avg}$ 250×g), then pipetted off and placed into labelled vials on ice and then frozen at −80° C. Samples were shipped on dry ice.

Tissue Collections: After blood collection the trachea and lung tissue were harvested. Briefly, the ventral side of the neck was cut to expose the thyroid and sternothyroid muscles. The muscles were gently teased apart to expose the larynx and trachea, A hemostat was used to close off the trachea (near the larynx) which then was cut just posterior to the larynx and the entire trachea, bronchial tree was removed with the lungs attached. The trachea was separated from the lungs. Tissue was not rinsed in saline. Each tissue sample was transferred to an individual labeled vial on ice and then frozen at −80° C. Samples were shipped on dry ice.

Observation of Animals

Mice were continually monitored for acute signs of toxicity for the first two hours following test compound administration. For groups of mice in the last time point (7 days), mice were monitored 2× daily prior to sacrifice and tissue collection. Body weights of individual mice were measured every Monday, Wednesday and Friday over the course of the study.

Data Collection

Actual time of blood collection (time of day), body weights and behavioural parameters as described in Experimental Design: Pharmacokinetic Sampling.

The following records were collected:
Manual Randomization by body weight
Individual body weights
Observations
Comments
Actual time of blood & tissue collection
Identity of tissue samples
Reasons/findings related to any premature termination of animals Observations of Animals Evaluation of Drug-Induced Stress—All animals were observed post administration, and at least once a day, more if deemed necessary, during the pre-treatment and treatment periods for mortality and morbidity. In particular, signs of ill health were based on body weight loss, change in appetite, and behavioral changes such as altered gait, lethargy and gross manifestations of stress. When signs of severe toxicity were seen, the animals were terminated ($CO_2$ asphyxiation) and a necropsy was performed to assess other signs of toxicity. The following organs were examined: liver, gall bladder, spleen, lung, kidney, heart, intestine, lymph nodes and bladder. Any other unusual findings were also noted.

Moribund animals were terminated for humane reasons and the decision to terminate was at the discretion of the animal care technician and the study director. These findings were recorded as raw data and the time of death will be logged on the following day.

In Vivo Mouse Model of Influenza

Animals

A mouse model of influenza was used for this study. 6-7 week old female mice (Balb/C—*Mus musculus*), Mice were given adapted HK1 influenza virus at 1250 pfu per mouse. Challenge doses were 3×LD50 determined in in vivo titration studies. Animals were housed in level 2 containment.

Sequence of Activities in the Study

| | Time | | |
|---|---|---|---|
| Week | Day | Hour | Activity |
| 1 | 1 | −2 | First treatment |
| | | 0 | Inoculate with virus |
| | | 4 | Second treatment |
| | | | Observe animals twice daily |
| | 2 | 16 | Third treatment |
| | | 24 | Fourth treatment |
| | | | Observe animals twice daily |
| | 3 | 40 | Fifth treatment |
| | | 48 | Sixth treatment |
| | | | Observe animals twice daily |
| | 4 | 64 | Seventh treatment |
| | | 72 | Eighth treatment |
| | | | Observe animals twice daily |
| | 5 | 88 | Ninth treatment |
| | | 96 | Tenth treatment |
| | | | Observe animals twice daily |

-continued

| Time | | | |
|---|---|---|---|
| Week | Day | Hour | Activity |
| | 6 | 112 | Eleventh treatment |
| | | 120 | Twelfth treatment |
| | | | Observe animals twice daily |
| 2 | 7-14 | | Observe animals daily |
| 3 | 14-21 | | Observe animals daily |

Intranasal Dose Administration

Mice were anesthetized with isoflurane 2% and 2 L/O2/min until the absence of a toe pinch reflex. Animals were restrained in an upright position and using a micropipette, animals were instilled with 10 μL of the compounds into each nostril. The mice were briefly restrained during the instillation procedure for approx. 20 seconds and the rate of release should be adjusted to allow the mice to inhale the compounds without forming bubbles. The mice were placed back in the anesthetic chamber in an inverted position for an additional 2 minutes or until their breathing returned to normal.

Intranasal Virus Inoculation

Mice were anesthetized with isoflurane 2% and 2 L/O2/min until the absence of a toe pinch reflex. Animals were restrained in an upright position and using a micropipette, animals were instilled with 10 μL of a virus preparation containing 3,000 pfu of influenza A virus, A/HK/1/68 (H3N2) in to each nostril (total inoculum of 1,250 pfu per animal). The virus was prepared as a suspension in serum-free DMEM. The mice were briefly restrained during the instillation procedure for approx. 20 seconds and the rate of release should be adjusted to allow the mice to inhale the compounds without forming bubbles. The mice were placed back in the anesthetic chamber in an inverted position for an additional 2 minutes or until breathing returned to normal.

Data Collection

The following records were collected:
  Manual randomization by body weight
  Individual body weights
  Observations
  Comments
  Reasons/findings related to any premature termination of animals Evaluation of Drug or Disease Induced Stress All animals were observed post administration, twice a day during treatment periods and once every day thereafter for mortality and morbidity. Signs of ill health included body weight loss, change in appetite, difficulty in breathing and behavioral changes such as altered gait/posture, lethargy and gross manifestations of stress. At the sign of severe illness (determined by >15% weight loss), the animals were called endpoint and terminated ($CO_2$ asphyxiation).

Moribund animals were terminated for humane reasons and the decision to terminate was at the discretion of the animal care technician and the study director. These findings were recorded as raw data and the time of death were logged on the following day.

Cell-Based Assay of Influenza Anti-Viral Activity for 3' Equatorial F Compounds

Compounds were tested for antiviral activity using a cell based assay, which consists of making serial 2-fold dilutions of the antiviral compounds (from 1:2 to 1:4096 in MegaVir medium in enough volume for the number of viruses tested—60 uL per virus), to which is added 100 infectious units of the specific influenza virus and the preparations are transferred to monolayers of MDCK cells in a microtitre plate. The assay was carried out on a 96-well microtitre plate. The plate is monitored for the development of influenza cytopathic effects from days 3 to 5 post infection. Antiviral activity is determined by the inhibition of development of cytopathic effects. The highest dilution of the compound at which the monolayers are intact is taken as the end-point. 4-G diF SA, Zanamivir, Oseltamivir, and Peramivir were used as controls.

Dilution Preparations:
11. In row A on a clean 96-well microtitre plate, prepare 2-fold serial dilutions of antiviral compounds from 1:2 to 1:4096 in MegaVir medium in enough volume for the number of viruses tested (60 uL per virus).
12. Transfer 55 uL of the 2-fold dilution series to a clean row in the 96-well microtitre plate.
13. To the 55 uL dilution series, add 55 uL of diluted influenza virus (at 100 $TCID_{50}$ per 25 ul). Also add virus to positive control wells.
14. To the now 110 uL mixture, add 55 uL of 4×TPCK-treated trypsin. Add trypsin also to positive and negative control wells. Mix well.
15. Prepare also 2-fold serial dilutions from 1:2 to 1:256 for the inoculating virus in MegaVir medium for back titration.

Plate Inoculation:
16. In a 96-well microtitre plate containing confluent monolayers of MDCK cells in ~200 uL MegaVir medium, transfer 75 uL of the mixture to 2 respective rows as duplicates.
17. Transfer 50 uL of the positive control, and 25 uL of negative controls to respective wells.
18. Transfer also 25 uL of the virus back titration in duplicates.
19. Therefore in each well:
    a. Samples: 25 uL compounds+25 uL virus+25 uL trypsin
    b. Positive control: 25 uL virus+25 uL trypsin (no compounds)
    c. Negative control: 25 uL trypsin (no compounds or virus)
    d. Back titration: 25 uL virus
20. The plates are incubated at 37 C in a $CO_2$ incubator for 3 days, then observed for the appearance of cytopathic effects on day 3 and day 5.

Viruses for 3' Equatorial F Compounds

The mutants were generated by producing viruses in derivatives of Zanamivir, all of which still had the 4-guanidinium group. Each of the mutants have mutations at E119. E119 interactions are significant for high affinity binding of NAIs, but each substitution often only affects binding of a subset of the inhibitors. It is already known that E119G confers Zanamivir and peramivir resistance, but not Oseltamivir, which is though to be due to altered interactions with the guanidinium group, and E119V confers Oseltamivir and 4-aminoNeu5Ac2en resistance, but not to Zanamivir or Peramivir.

Wild Type Viruses:

*A/Auckland/3/2009 (pandemic H1N1)
*B/Florida/4/2006
*A/Solomon Islands/3/2006 (seasonal H1N1)
G70C H1N9 wt
E119G Fukui H3N2 wt
sH1N1/01 $H_{274}Y$
sH1N1/08 wt
B/Perth wt Mutant Viruses:
*A/Auckland/3/2009 mutant 1 E119K
*B/Florida/4/2006 mutant 1 E117D (E119D N2 numbering)
*A/Solomon Islands/3/2006 mutant E119A
G70C H1N9
Fukui H3N2 E119V
sH1N1/01 $H_{274}$Y
sH1N1/08 $H_{274}$Y
B/Perth D197E
*provided by Biota Holdings Limited

EXAMPLES

Further embodiments are described with reference to the following, non-limiting, examples.

Example 1

Viral Sialidase Enzyme Assays

Incubation of influenza sialidase with different concentrations of the various compounds resulted in time-dependent decreases in enzyme activity, as expected for mechanism-based inhibitors, and as shown for compound 4 in FIGS. 3A and B. FIGS. 3A and 3B show time-dependent inactivation of influenza sialidase (subtype N9) by compound 4. The enzyme was incubated with the indicated concentrations of compound 4, and aliquots assayed with 0.5 mM CF3MUSA. Inactivation by compound 4 at indicated concentration (3A), and re-plot of pseudo-first order inactivation kinetic constants (ki obs) versus concentration of compound 4 (3B).

All 3-fluorosialyl fluorides showed excellent inactivation profiles against influenza sialidase at 30° C. except compound 8, and the half time for the full inactivation of the sialidase was estimated as ca. 10 min for all amine derivatives (compounds 4, 7, 9, 11, and 12) (summary in Table 4). Interestingly, 4-aminated compound 4 and 4-guanylated compound 12 showed good inactivation values ($k_i/K_d$=25 $min^{-1}$ $mM^{-1}$ for compound 4 and $k_i/K_d$=24 $min^{-1}$ $mM^{-1}$ for compound 12). Furthermore, compounds 4 and 12 showed slow reactivation in buffer solution at the same temperature with the half time for the full reactivation of the inactivated sialidase being determined as 4.8 h for compound 4 and 6.7 h for compound 12. Accordingly, the 3-fluorosialylenzyme intermediate very stably blocked the active site in influenza sialidase and their effective $K_i$s were in the nanomolar range (93 nM for compound 4 and 70 nM for compound 12).

Inactivation parameters for 2,3-Difluorosialic acid, (23DFSA) and the 4-azide compound 8 could not be measured at 30° C. due to fast hydrolysis of sialylenzyme intermediate. Thus, the kinetic values for these two inhibitors were measured at 4° C., and the estimated inactivation numbers were given. The $k_i/K_d$ value of compound 23DFSA was determined as 196 $min^{-1}$ $mM^{-1}$, and 4-azide compound 8 and 4-amine compound 4 showed 26-fold lower kinetic values at 4° C. ($k_i/K_d$=7.5 $min^{-1}$ $mM^{-1}$ for compound 8 and 7.3 $min^{-1}$ $mM^{-1}$ for compound 4). Although the 4-amine derivatives showed lower inactivation kinetic values, these compounds were revealed as much better inhibitors than the 4-hydroxylated derivative (23DFSA) due to their very slow reactivation.

TABLE 4

Kinetic parameters for the reaction of influenza sialidase with 3-fluorosialyl fluorides.[a]

| Compound | $k_i/K_d$ ($min^{-1}mM^{-1}$) | $K_d$ (mM) | $t_{1/2\ (inactivation)}$ (mM) | $k_{hyd}$ ($min^{-1}$) | $K_i$ (nM) |
|---|---|---|---|---|---|
| 23DFSA | 196[b] | ND[b] | ND[b] | ND[b] | ND[b] |
| C4 Bn | 0.61 | 0.306 | 3.7 | 0.0025 | 4080 |
| 8 | 7.5[b] | 0.240[b] | 0.4[b] | ND[b] | ND[b] |
| 9 | 0.34 | 1.016 | 1.9 | ND | ND |
| 11 | 0.53 | 0.397 | 3.2 | ND | ND |
| 7 | 4.1 | 0.014 | 11.7 | ND | ND |
| 4 | 25 (7.3)[b] | 0.004 | 6.4 | 0.0024 | 93.2 |
| 12 | 24 | 0.009 | 3.1 | 0.0017 | 70.4 |

[a]All the experiments were carried out in 20 mM TRIS/50 mM $CaCl_2$ buffer, pH 7.6 containing 0.1% BSA at 30° C.
[b]The kinetic values were collected at 4° C.
ND = not determined.

Example 2

Human Sialidase Enzyme Assays

Incubation of different concentrations of each compound with human sialidase resulted in no inactivation of the human sialidase even at very high concentrations (10 mM) of compound demonstrating the specificity of the compounds for influenza sialidases.

Example 3

Cytoprotection Assays with Influenza A Strains

The candidate inhibitors (compounds 4, 5, 7-9 and 11-13) were tested against Zanamivir and/or 2,3-DFSA for their cytopathic effect (CPE) against two influenza A strains. It is important to note that, although the present Cytoprotection assay is a good qualitative indicator of antiviral activity, the results are often variable (as note by others, Tisdale M. (2000)) and caution exercised when doing a quantitative analysis.

TABLE 5

The activity of compounds against influenza A/Brisbane/10/2007 (H3N2)

| | Replicate 1 | | Replicate 2 | | Toxicity | |
|---|---|---|---|---|---|---|
| Compound | Cytoprotective effect (ng/mL) | Relative activity | Cytoprotective effect (ng/mL) | Relative activity | (ug/mL) | Relative toxicity |
| Zanamivir | 277.4 | 1.0 | 369.9 | 1.0 | 568 | 1.0 |
| 4 (DFSA-4NH2) | 6.9 | 40.0 | 9.2 | 40.2 | 3.6 | 160.0 |
| 5 (N3-105ET) | 7.6 | 36.4 | 7.6 | 48.6 | 125.0 | 4.5 |

TABLE 5-continued

The activity of compounds against influenza A/Brisbane/10/2007 (H3N2)

| Compound | Replicate 1 Cytoprotective effect (ng/mL) | Relative activity | Replicate 2 Cytoprotective effect (ng/mL) | Relative activity | Toxicity (ug/mL) | Relative toxicity |
|---|---|---|---|---|---|---|
| 7 (N3-102ET) | 122 | 2.3 | 61.0 | 6.1 | 7.8 | 72.7 |
| 12 (DFSA-4Gu) | 55.5 | 5.0 | 74 | 5.0 | 0.9 | 640.0 |
| 13 (N3-106ET) | 44.4 | 6.3 | 44.4 | 8.3 | 1.4 | 400.0 |
| 11 (N3-107AC) | 1598 | 0.2 | — | — | 102.3 | 5.6 |
| 8 (N3-109N3) | 104.3 | 2.7 | — | — | 53.4 | 10.6 |
| 9 (N3-111AMD) | 117.6 | 2.4 | — | — | 7.5 | 75.5 |

TABLE 6

The activity of compounds against influenza A/Denver/1/57 (H1N1)

| Compound | Cytoprotective effect (ng/mL) | Relative activity |
|---|---|---|
| Zanamivir | 4.3 | 1.0 |
| 4 (DFSA-4NH2) | 887.8 | 0.005 |
| 7 (N3-102ET) | 3906.3 | 0.001 |
| 5 (N3-105ET) | 488.3 | 0.009 |
| 12 (DFSA-4Gu) | 887.8 | 0.005 |
| 13 (N3-106ET) | 710.2 | 0.006 |
| 9 (N3-111AMD) | 3764.2 | 0.001 |
| 23DFSA | 4261.4 | 0.001 |

TABLE 7

The activity of compounds 4 and 12 against a variety of influenza A viruses and an Oseltamivir resistant strain (OsR)

| Virus (100 × TCID$_{50}$) | Trials | Antiviral compound Zanamivir [μM] | DFSA-4NH2 (compound 4) [μM] | DFSA-4Gu (compound 12) [μM] |
|---|---|---|---|---|
| A/Brisbane NML (H3N2) | 1 | 0.834$^B$ | 51.415$^B$ | 12.215$^B$ |
| A/Hong Kong (H3N2) | 1 | 20.026$^B$ | 1028.306$^B$ | 73.288$^B$ |
|  | 2 | 5.007$^B$ | 64.269$^B$ | 4.581$^B$ |
|  | 3 | 6.413$^B$ | >115.519$^C$ | 42.183$^C$ |
| A/Denver (H1N1) | 1 | <0.209$^A$ | <12.854$^A$ | <3.054$^A$ |
| A/New Caledonia (H1N1) | 1 | 0.417$^A$ | <12.854$^A$ | <3.054$^A$ |
| A/Brisbane NML (H1N1) | 1 | 6.675$^A$ | 102.831$^A$ | 6.107$^A$ |
|  | 2 | 8.344$^B$ | 411.323$^B$ | 3.054$^B$ |
|  | 3 | 2.138$^B$ | >115.519$^C$ | 4.474$^C$ |
| A/Brisbane 6770 (H1N1-OsR) | 1 | <0.209$^A$ | 12.854$^A$ | <3.054$^A$ |
|  | 2 | 0.039$^B$ | 9.640$^B$ | 0.382$^B$ |
|  | 3 | 0.013$^B$ | 2.410$^B$ | 0.382$^B$ |
|  | 4 | 0.025$^B$ | 3.971$^C$ | 0.300$^C$ |

Multiple experiments were performed on different days on some strains
$^A$Single measurement;
$^B$Mean of dual measurements;
$^C$Mean of six measurements TABLE 7 shows the concentration of antiviral (μM) at which a confluent monolayer of MDCK cells was protected over a 5 day period from cytopathic viral infection.

Example 4

Cytoprotection Assays with Influenza B Strains

The candidate inhibitors were tested against Zanamivir for their cytopathic effect (CPE) against two influenza B strains. It is important to note that, although the present Cytoprotection assay is a good qualitative indicator of antiviral activity, the results are often variable (as noted by others, Tisdale M. (2000)) and caution exercised when doing a quantitative analysis.

TABLE 8

The activity of compounds against influenza B/HongKong/5/72

| Compound | Cytoprotective effect (ng/mL) | Relative activity |
|---|---|---|
| Zanamivir | 2219 | 1.0 |
| 4 (DFSA-4NH2) | 1775.6 | 1.25 |
| 7 (N3-102ET) | 3906.3 | 0.57 |
| 5 (N3-105ET) | 976.6 | 2.27 |
| 12 (DFSA-4Gu) | 1775.6 | 1.25 |
| 13 (N3-106ET) | 710.2 | 3.13 |
| 9 (N3-111AMD) | 15056.8 | 0.15 |
| 23 DFSA | 34090.9 | 0.07 |

TABLE 9

The activity of compounds against influenza B/Florida/04/06

| Compound | Replicate 1 Cytoprotective effect (ng/mL) | Relative activity | Replicate 2 Cytoprotective effect (ng/mL) | Relative activity |
|---|---|---|---|---|
| Zanamivir | 2219 | 1.0 | 887 | 1.0 |
| 4 (DFSA-4NH2) | 947 | 2.3 | 1074 | 0.83 |
| 7 (N3-102ET) | 3267 | 0.67 | 3267 | 0.27 |
| 5 (N3-105ET) | 290 | 7.7 | 290 | 3.1 |

Example 5

In Vivo Pharmacokinetic (PK) Profile Study

The purpose of the study was to evaluate the pharmacokinetic profile of a novel fluorosialic compound (DFSA-4Gu), in comparison with Zanamivir by the intranasal route and to compare the pharmacokinetic profile of DFSA-4Gu when dosed by the intranasal and intravenous routes in the Balb/C mouse (*Mus musculus*).

4Gu)=1.07. The apparent half-lives of the two agents in the lung after intranasal dosing were also similar.

TABLE 10

Study Parameters

| Gp # | Group Name | # of Animals | Dose (mg/kg) | Admin. Route | Dose Volume (μL) | N per time point | Time-point |
|---|---|---|---|---|---|---|---|
| 1 | DFSA-IV | 23 | 1 | Intravenous | 200/20 g (10 μL/g) | 4 3 | 5, 15, 30 min, 1, 2 hr 7 d |
| 2 | DFSA-IN | 23 | 1 | Intranasal | 10 μL/nostril/15 g (0.67 μL/nostril/g) | 4 3 | 5, 15, 30 min, 1, 2 hr 7 d |
| 3 | ZAN-IN | 23 | 1 | Intranasal | 10 μL/nostril/15 g (0.67 μL/nostril/g) | 4 3 | 5, 15, 30 min, 1, 2 hr 7 d |

A PK study was conducted to evaluate DFSA-4Gu in mice, administered by IN and IV routes, and to evaluate Zanamivir administered by the IN route, all at 1 mg/kg in a single dose. Tissue levels and plasma levels for DFSA-4Gu were obtained and lung tissue levels for Zanamivir were obtained. Levels declined with apparent first order kinetics in all tissues by both routes. Comparison of DFSA-4Gu and Zanamivir by the IN routes showed that comparable compound exposure in the lung was observed with both agents.

Calculated PK Parameters

PK parameters calculated for DFSA-4Gu and Zanamivir after intranasal dosing with a single 1 mg/kg dose.

TABLE 11A

Calculated PK Values

| Tissue | Compound | AUC (ng × min/L) | $T_{1/2}$ (min) | $C_{initial}$ (ng/mL) |
|---|---|---|---|---|
| Plasma | DFSA-4Gu | 76433 | 17.3 | 4954 |
| Trachea | DFSA-4Gu | 421865 | 28.1 | |
| Lung | DFSA-4Gu | 236814 | 22.2 | |
| Lung | Zanamivir | 254089 | 19.1 | |

PK parameters calculated for DFSA-4Gu after intravenous dosing with a single 1 mg/kg dose.

TABLE 11B

Calculated PK Values

| Tissue | Compound | AUC (ng × min/L) | $T_{1/2}$ (min) | $C_{initial}$ (ng/mL) |
|---|---|---|---|---|
| Plasma | DFSA-4Gu | 88202 | 8.3 | 9480 |
| Trachea | DFSA-4Gu | 24749 | 9.4 | |
| Lung | DFSA-4Gu | 25307 | 14.2 | |

The apparent half-life for the compounds was longer after intranasal dosing than after intravenous dosing. As well the exposure, expressed as AUC for DFSA-4Gu was increased in trachea and lung by intranasal dosing, relative to intravenous dosing with AUC ratios (IN/IV) for lung=9.3 and for trachea=17.0.

The AUC in lung after intranasal dosing of Zanamivir and DFSA-4Gu were similar, AUC(Lung) (Zanamivir/DFSA- Example 6

In Vivo Murine Model of Influenza Infection

The in vivo efficacy of Zanamivir, DFSA-4Gu & DFSA-4NH2 was tested in a mouse model of influenza (HK1). Compounds were compared to Zanamavir, whereby animals received a single intranasal dose of drug prior to infection and were given follow-up doses twice per day for a total of six days. Mortality due to infection was set at 15% weight loss after which animals were euthanized. Survival of animals was significantly extended in groups that received a 1 mg/Kg dose of DFSA-4GU and Zanamavir, as compared to the untreated control group. Similarly, treatment with DFSA-4NH2 did somewhat extend survival as compared to the untreated control group. However, drug treatments did not prevent mortality as all treated animals eventually reached endpoint due to influenza infection. Although these results are promising, the use of a different virus strain or an increased dose of drugs may alter the survival.

TABLE 12

Experimental Groups and Treatments

| Gp # | Group Name | Test Article | N | Doses (mg/kg/d) | Virus Strain |
|---|---|---|---|---|---|
| 1 | PR8-DFSA-4Gu | DFSA-4Gu | 10 | 1 | A/Hong Kong/1/68 (H3N2) |
| 2 | PR8-DFSA-4NH2 | DFSA-4NH2 | 10 | 1 | |
| 3 | PR8-ZAN | Zanamivir | 10 | 0.1 | |
| 4 | PR8-ZAN | Zanamivir | 10 | 1 | |
| 5 | PR8-Untreated | Saline | 10 | N/A | |
| 6 | DFSA-4NH2-Control | DFSA-4NH2 | 5† | 1 | None |
| 7 | DFSA-4Gu-Control | DFSA-4Gu | 5 | 1 | |
| | Total N: | | 60 | | |

†The original protocol called for N = 3 for each healthy control group (Groups 6 and 7 in Table 6). In the execution of the study, N = 5 were used in these groups, increasing the total animal number to 60.

TABLE 13

Survival rates of animals on days 3, 4, 5, 6, 7 and 8 post infection. TABLE 13 shows the number of animals remaining in each group. N = 10 for all groups except groups 6 and 7 (n = 5).

| | Day 3 pm | Day 4 am | Day 4 pm | Day 5 am | Day 5 pm | Day 6 am | Day 6 pm | Day 7 am | Day 7 pm | Day 8 am | Day 8 pm |
|---|---|---|---|---|---|---|---|---|---|---|---|
| Group 1 HK1-DFSA-Gu-(1 mg/kg) | 10 | 10 | 8 | 7 | 6 | 5 | 4 | 3 | 1 | 1 | 0 |
| Group 2 HK1-DFSA-4NH2-(1 mg/kg) | 10 | 10 | 3 | 2 | 1 | 0 | 0 | 0 | 0 | 0 | 0 |
| Group 3 HK1-ZAN-(0.1 mg/kg) | 10 | 9 | 2 | 1 | 1 | 0 | 0 | 0 | 0 | 0 | 0 |
| Group 4-HK1-ZAN-(1 mg/kg) | 10 | 10 | 9 | 5 | 3 | 2 | 1 | 0 | 0 | 0 | 0 |
| Group 5 Untreated | 10 | 10 | 4 | 1 | 0 | 0 | 0 | 0 | 0 | 0 | 0 |
| Group 6 DFSA-4NH2-Control | 5 | 5 | 5 | 5 | 5 | 5 | 5 | 5 | 5 | 5 | 5 |
| Group 7 DFSA-4GU-Control | 5 | 5 | 5 | 5 | 5 | 5 | 5 | 5 | 5 | 5 | 5 |

TABLE 14

Mean % weight loss per group on day 4 (am) post infection. This time point was selected because many animals were on the verge of reaching endpoint, but most groups still had 10 animals.

| | P-value[1] | % weight loss mean +/− SD |
|---|---|---|
| Group 1 HK1-DFSA-4Gu-1.0 | 0.01 | 10.75 +/− 4.87 |
| Group 2 HK1-DFSA-4NH2-1.0 | 0.14 | 16.02 +/− 2.07 |
| Group 3 HK1-ZAN-0.1 | 0.06 | 16.73 +/− 2.62 |
| Group 4-HK1-ZAN-1.0 | 0.01 | 12.24 +/− 2.34 |
| Group 6 DFSA-4NH2-Control | 0.00 | 2.68 +/− 1.76 |
| Group 7 DFSA-4GU-Control | 0.00 | 4.72 +/− 2.78 |
| Group 5 Untreated | | 15 +/− 2.06 |

[1]P-value determined by student's T-test in which each group was individually compared to the mean of untreated group #7. A p-value below 0.05 was considered statistically significant.

With regards to the above results, and the potential alteration in protocol, the use of a different virus strain, a different end point, or an increased dose of drugs may be justified. For example, another mouse adapted virus strain such as A/PR/8/34 may produce different results. Also, an endpoint of 15% weight loss may be too low, whereby animals may still recover after losing 20% or more. For example Bantia et al. (2001) reported recovery of Zanamavir treated animals after more than 20 percent weight loss. Similarly, a higher dose of drug may be required to achieve complete protection. For example, Levena et al. (2001), the authors required doses of Zanamavir at 10 and 50 mg/kg/day before they observed a protective effect.

Figure 2:
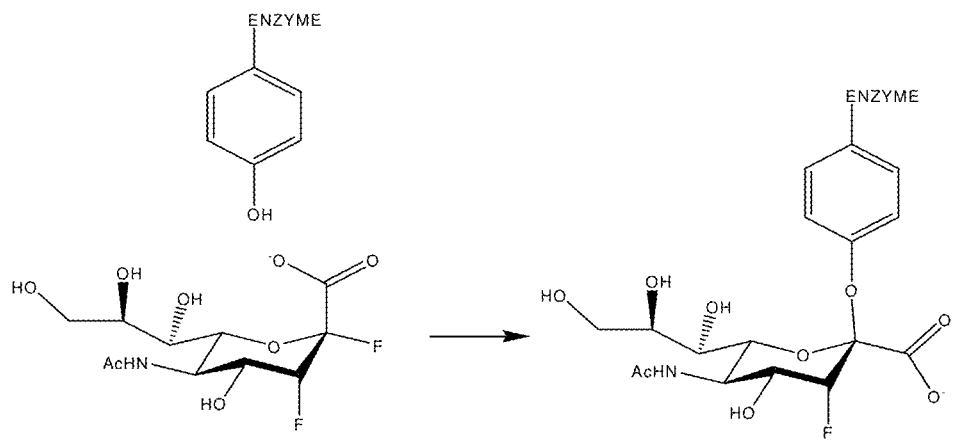
FIG. 2 shows inactivation of a neuraminidase by 2,3-difluorosialic acid (1).
Figure 3A:
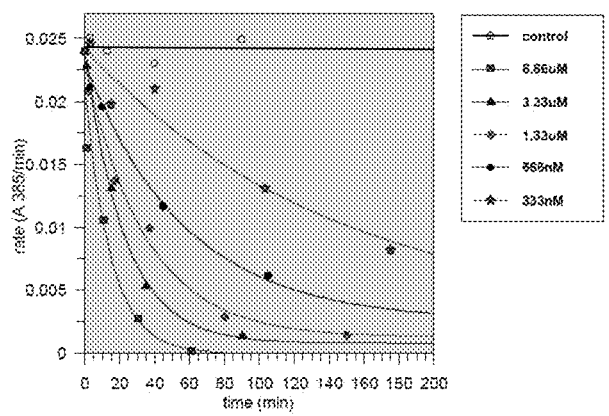
FIGS. 3A & 3B show a time-dependent inactivation of influenza sialidase (subtype N9) by compound 4, indicated by concentration (3A), and re-plot of pseudo-first order inactivation kinetic constants ($k_{i\ obs}$) versus concentration of compound 4 (3B).
Figure 3B:
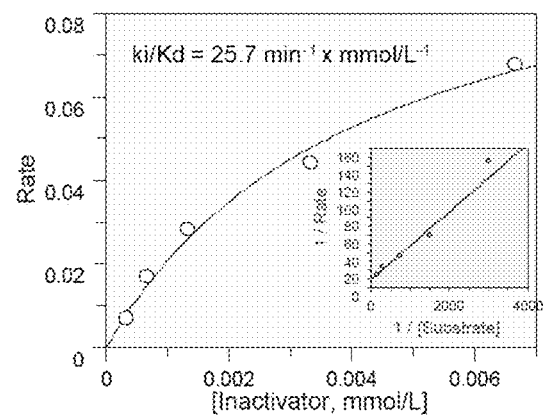
Figure 4A:
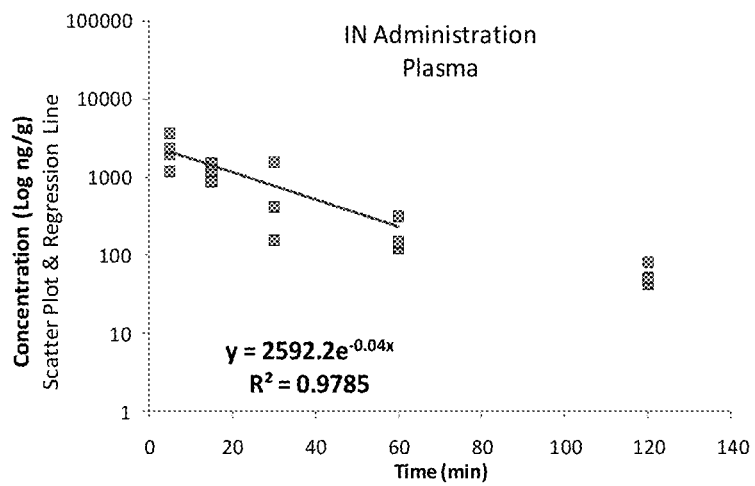
FIGS. 4A & 4B show DFSA-4Gu Plasma levels after IV and IN administration.
Figure 4B:
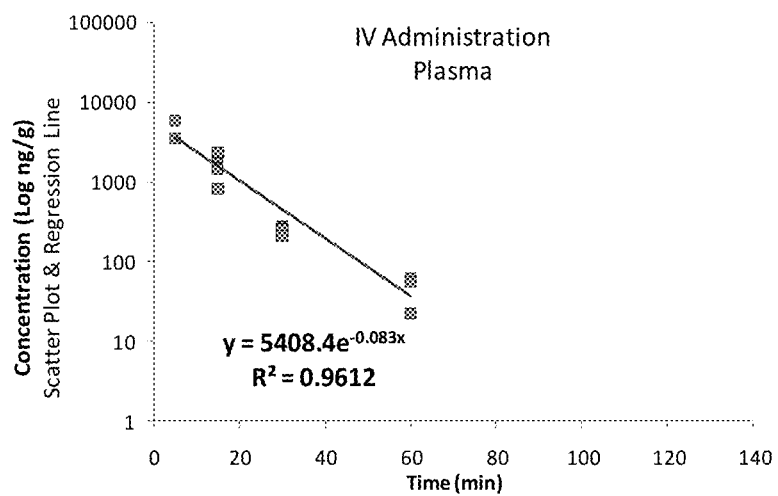
Figure 5A:
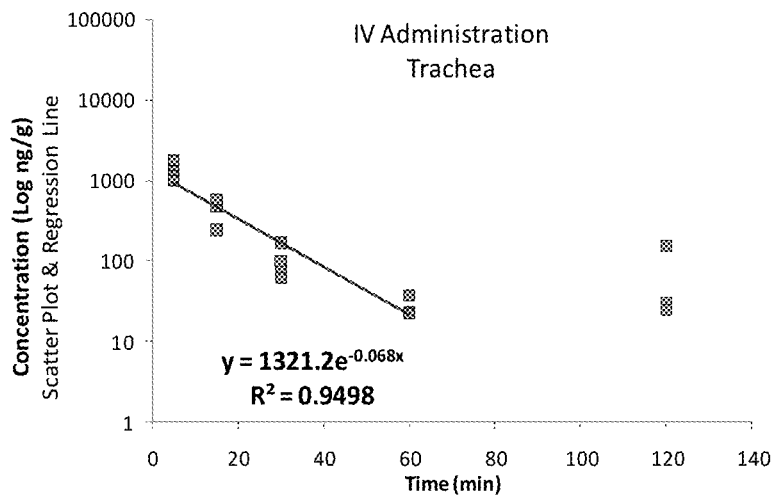
FIGS. 5A, 5B, & 5C show DFSA-4Gu Trachea levels after IV and IN administration.
Figure 5B:
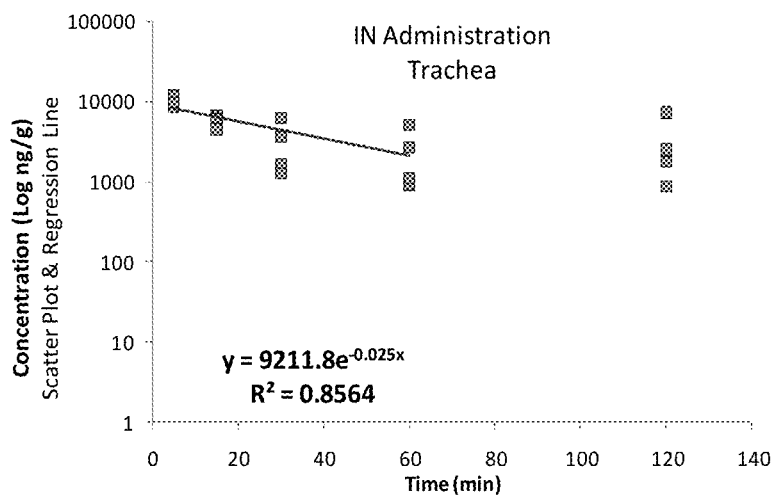
Figure 5C:
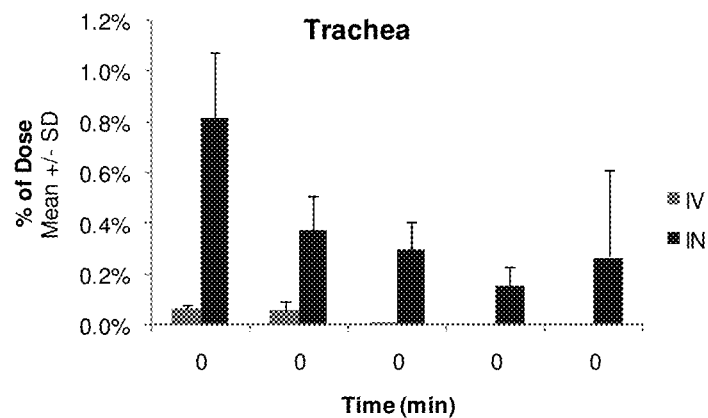
Figure 6A:
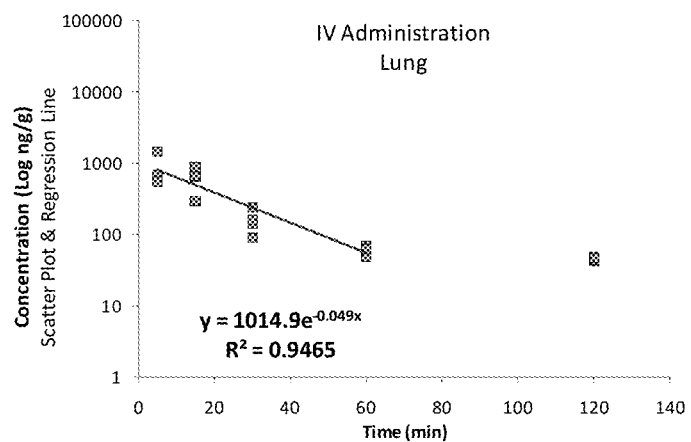
FIGS. 6A, 6B, & 6C show DFSA-4Gu Lung levels after IV and IN administration.
Figure 6B:
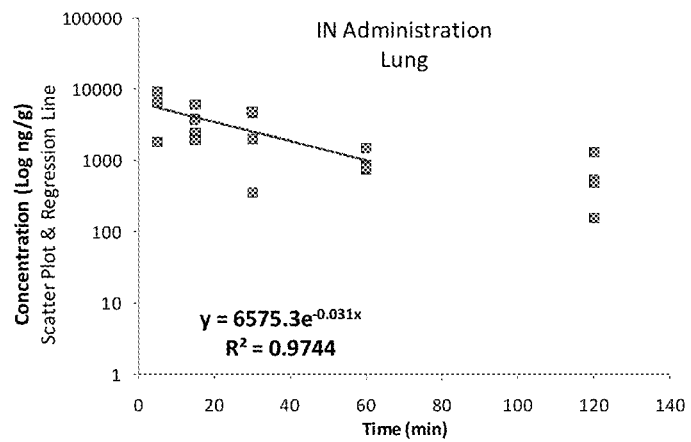
Figure 6C:
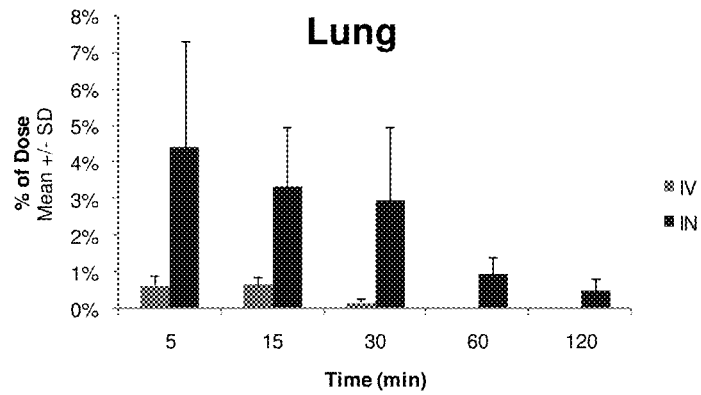
Figure 7:
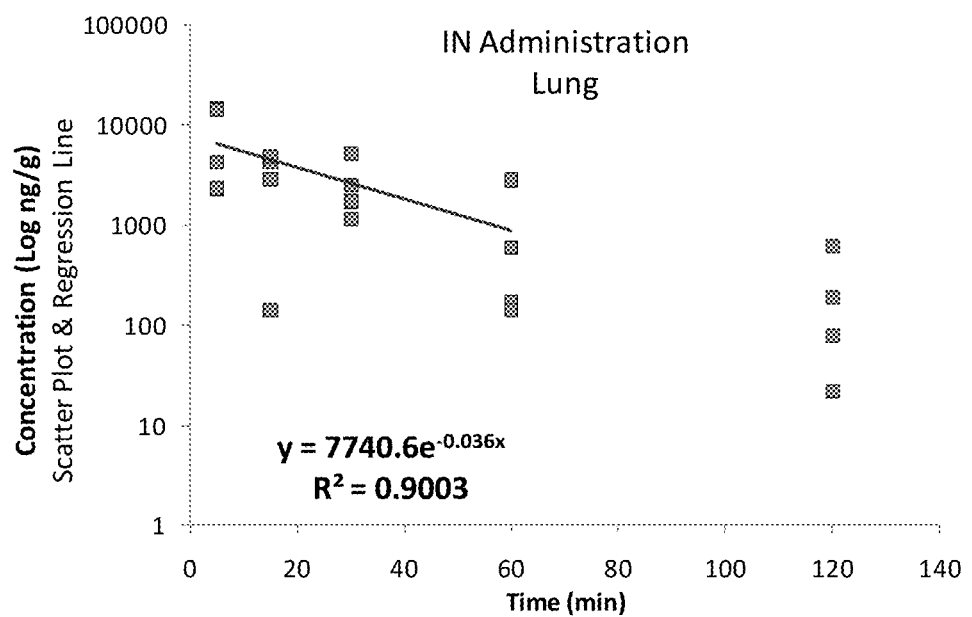
FIG. 7 shows a Zanamivir Lung levels after IV and IN administration.
Figure 8:
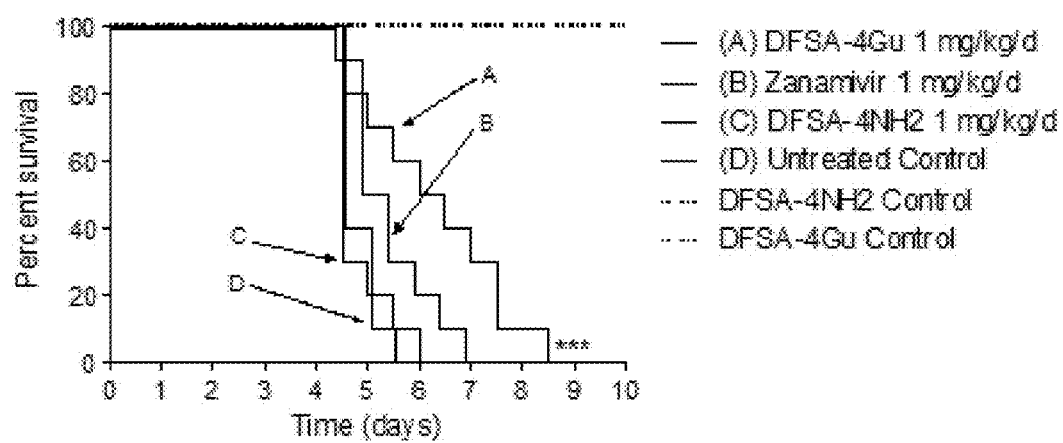
FIG. 8 shows a survival plot of mice infected with HK1 $H_2N3$ Influenza A virus and treated with neuraminidase inhibitors.

Fluorinated compounds of the class described in this invention are inhibitors of a range of glycosidases, and specific with respect to their target enzymes. These compounds are mechanism-based in their inhibitory action. They bind to the enzyme like the normal substrate and undergo the first step of catalysis (intermediate formation) like the natural substrate, but then only very slowly undergo the second step (turnover via hydrolysis). Importantly, this mechanism-basis inhibition should make resistance formation by viruses more difficult. Since the inhibitors are mechanism-based, any mutations in the viral enzyme that reduce the inhibition must necessarily reduce the efficiency of the enzyme on the natural substrate. FIG. 2 shows an example of neuraminidase inhibition by 3-fluorosialyl fluoride (1, 23DFSA) (note: sialic acid numbering is different from that of normal sugars due to the anomeric carboxylate).

The fluorosialics differ fundamentally from Zanamivir and Oseltamivir in two major ways. Zanamivir and Oseltamivir are reversibly binding inhibitors that interact with the enzyme active site very tightly due to their flattened, cyclic conformation. Their binding mode likely imitates the transition state conformation of the sugar during hydrolysis. They are therefore transition state mimics. The fluorosialics, by contrast, contain no double bond thus adopt a regular chair conformation. They react with the enzyme as if they are substrates and form a covalent bond with the active site nucleophile, and only hydrolyse to products very slowly. They derive their very high efficacies from the long-lived nature of the intermediate formed.

Due to this completely different mode of action it was not evident that incorporation of an amine or guanidine substituent would increase their effectiveness since the sugar ring has a very different conformation in the two cases: the amine/guanidine would be presented in a very different manner in the two cases, thus likely interacts quite differently. Even more importantly, the major efficacy of the fluorosialics derives from the formation of a relatively long-lived covalent intermediate. It was not at all evident that incorporation of the 4-amine/guanidine in place of the 4-hydroxyl would slow down the hydrolysis of this intermediate (deglycosylation) much more than it slowed the formation of the intermediate (glycosylation) with the result of a much longer-lived intermediate thus a higher efficacy inhibitor.

Furthermore, comparative binding of these wild type and mutant viruses against Zanamivir, Oseltamivir, 4-G diF SA and 4-G3Feq diF SA was conducted. Based on $IC_{50}$ kinetics and reactivation experiments previously conducted, it was known that these mutant viruses showed resistance to Zanamivir, but also to Peramivir and Oseltamivir, with rapid binding/dissociation of all.

TABLE 15

2,3-Fluorinated Glycosides having both a 3 equatorial Fluorines

| Compound | Structure |
|---|---|
| 4-G 3 F equatorial diF SA (4-G 3Feq diFSA) Compound 4G3Feq | [structure with guanidino, CO2−, two F atoms] |
| | [alternative representation with COOH] |
| 4-NH$_2$ 3 F equatorial diF SA (2F3F4NH$_2$) Compound 4NH$_2$3Feq | [structure with H$_2$N, CO$_2^-$, two F atoms] |

TABLE 15-continued

2,3-Fluorinated Glycosides having both a 3 equatorial Fluorines

| Compound | Structure |
|---|---|
| | [alternative representation with H$_2$N, CO$_2$H, two F atoms] |
| | (alternative) |

Even though the tested viruses were the most resistant viruses handled to date, the viruses were surprisingly fit. Although the NA activity of each is very low, <10% of wild types, they still showed sufficient NA to grow to high titres in cell culture. Fitness in animals is yet to be determined.

Since some of the promising diF SA compounds have a 4-guanidino group it was of interest whether the viruses would also show resistance to our 4-guanidino compounds. Furthermore, this would potentially provide an indication of the relative roles of the formation of the covalent linkage and the interactions with the guanidinium group in terms of high affinity binding of the 4-G diF (control) and 4-G3Feq diF SA (test) compounds.

Example 7

Cytoprotection Assays with Various Viral Strains

TABLES 16-19 show the concentrations of control and test antivirals (μM) at which a confluent monolayer of MDCK cells was protected over a 5 day period from cytopathic viral infection by a variety of viral strains. The test antiviral for the below tables is 4-G3Feq diF SA with a 3' equatorial F.

TABLE 16

Effects of mutations at E119A, D, K on sensitivity to inhibitors (IC$_{50}$ μM)

| nM | B/Florida wt | B/Florida E119D | Fold Res | Sol Isl sH1N1 wt | Sol Isl sH1N1 E119A | Fold Res | Auckland pH1N1 wt | Auckland pH1N1 E119K | Fold Res |
|---|---|---|---|---|---|---|---|---|---|
| Zanamivir | 3.9 | >10,000 | ≥10,000 | 2.2 | >10,000 | ≥100,00 | 0.6 | >100,000 | ≥100,000 |
| Oseltamivir | 22.6 | 1205 | 53 | 1.0 | 419 | 419 | 0.2 | 147 | 613 |
| 4-G diF SA | 6.6 | 1515 | 229 | 181 | >10,000 | >1000 | 284 | >100,000 | >1000 |
| 4-G3Feq diF SA | 2.0 | 27 | 13 | 4.7 | 130 | 27 | 4.0 | >100,000 | ≥10,000 |

The results shown in TABLE 16 are consistent with previous testing of other panels of viruses with 4-G diF SA. However, the 4-G3Feq SA has a lower IC$_{50}$ than the 4-G diF SA for many of the resistant strains.

The E119K mutation appears to confer some resistance to both 4-G diF SA and 4-G3Feq diF SA, but less so to Oseltamivir (4-NH$_2$), suggesting that the interactions of the 4-guanidinium group are potentially significant to high affinity binding of not only the established NAIs but also to both 4-G diF SAs. The most significant difference in resistance profiles was seen for the 4-G3Feq SA with the E119A mutation, there is >10,000-fold resistance to the other 3 drugs, but only 27-fold to the 4-G3Feq. Thus the 3F in the equatorial position results in significantly different binding behaviour for the 4-G diF SA compared to the other inhibitors with a 4-G group.

For the E119D there is lower resistance with the 4-G3Feq SA than the 4-G diF SA, and importantly also several orders of magnitude lower resistance than to Zanamivir. Since the E119D is significantly less resistant to 4-G diFeq SA than to Zanamivir, this suggests the guanidinium in the fluorosialics is less likely to select for resistant strains than that in zanamivir, likely due to the different (transient covalent) mode of action.

TABLE 17

Effects of mutations at E119G, V on sensitivity to inhibitors (IC$_{50}$ µM)

| | G70C H1N9 wt | G70C H1N9 E119G | Fold resistance | Fukui H3N2 wt | Fukui H3N2 E119V | Fold resistance |
|---|---|---|---|---|---|---|
| Zanamivir | 2.7 | 678 | 248 | 3.8 | 3.4 | 0.9 |
| Oseltamivir | 2.8 | 2.9 | 1.1 | 1.7 | 260 | 155 |
| 4-G diF SA | 66.7 | 1433 | 21 | 2006 | 998 | 0.5 |
| 4-G3Feq diF SA | 136 | 17.3 | 0.1 | 24.9 | 2.4 | 0.1 |

The E119G mutation appears to confer a high level resistance to Zanamivir only, confers 20-fold resistance to 4G diF SA, whereas the 4-G3Feq SA actually appears to bind better in the mutant than in the wild type.

The E119V mutation appears to confer a high level resistance to Oseltamivir, but does not confer resistance to the 4G diF SA, Zanamivir, or 4-G3Feq diF SA.

TABLE 19

Effects of D197E mutation on sensitivity to inhibitors (nM)

| | B/Perth wt | B/Perth D197E | Fold resistance |
|---|---|---|---|
| Zanamivir | 8.9 | 257.5 | 28.9 |
| Oseltamivir | 104.4 | 708.0 | 6.8 |
| 4-G diF SA | 54.0 | 161.9 | 3.0 |
| 4-G3Feq diF SA | 4.5 | 8.0 | 1.8 |

Mutations at D197 appear to confer cross resistance to known NAIs due to altered interactions with the adjacent $R^{152}$ and the N-acetyl group on the ring. However, the 4-G3Feq SA does not appear to be affected by this interaction.

Example 8

Comparison of 3' Axial with 3' Equatorial Compounds on H1N1 Viral Strains

TABLE 20

Comparison of 2 Equatorial/3 Axial and 2 Equatorial/3 Equatorial Compounds with Both 4 Gu and 4 NH$_2$ in H1N1.

| | H1N1 OsR | | | H1N1 | | |
|---|---|---|---|---|---|---|
| | 2F3F4Gu | | 2F3F4NH$_2$ | 2F3F4Gu | | 2F3F4NH$_2$ |
| | 2eq3ax | 2eq3eq | 2eq3eq | 2eq3ax | 2eq3eq | 2eq3eq | 2eq3ax |
| ki (min$^{-1}$) | 0.075 ± 0.002 | 1.5 ± 0.16 | 4.7 ± 0.1 | 0.094 ± 0.002 | 2.0 ± 0.3 | 0.79 ± 0.27 | 0.50 ± 0.03 |
| Ki (µM) | 0.47 ± 0.06 | 0.50 ± 0.08 | 5.5 ± 0.2 | 0.25 ± 0.026 | 0.35 ± 0.19 | 0.23 ± 0.17 | 2.90 ± 0.72 |
| ki/Ki (min$^{-1}$/µM) the ki/Ki | 0.16 | 3.0 | 0.85 | 0.37 | 5.8 | 3.5 | 0.18 |

TABLE 18

Effects of H274Y mutation on sensitivity to inhibitors (IC$_{50}$ nM)

| | sH1N1/01 wt | sH1N/01 H274Y | Fold resistance | sH1N1/08 wt | sH1N1/08 H274Y | Fold resistance |
|---|---|---|---|---|---|---|
| Zanamivir | 1.9 | 2.2 | 1.2 | 1.0 | 2.0 | 2.0 |
| Oseltamivir | 3.1 | 2440 | 781 | 3.0 | 2000 | 667 |
| 4-G diF SA | 115.4 | 217 | 1.9 | 136 | 265 | 1.9 |
| 4-G3Feq diF SA | 12.6 | 43.5 | 3.5 | 6.8 | 43.2 | 6.4 |

4G diF SA or 4-G3Feq SA appear to still be effective against the H274Y mutation which confers high level Oseltamivir resistance, but not to Zanamivir.

TABLE 21

Shows Reactivation Data for 2 Equatorial 3 Axial and 2 Equatorial 3 Equatorial Compounds with Both 4Gu and 4NH$_2$.

| Strain | Inactivator | Half life for reactivation (hours) |
|---|---|---|
| H1N1 OsR | 2eq3ax4Gu | 116 |
| H1N1 OsR | 2eq3eq4Gu | 9 |
| H1N1 OsR | 2eq3eq4NH2 | 2 |
| H1N1 NML | 2eq3eq4NH2 | 4 |

TABLE 20 shows formal kinetic data for inactivation of H1N1 and its Oseltamivir resistant mutant. The ki/Ki value is generally known as the specificity parameter, thus is the most readily interpreted. For both strains the 2 equatorial/3 axial guanidine, the 2 equatorial/3 equatorial-fluoro guanidine, and the 2 equatorial/3 equatorial-fluoro amine derivatives were tested, but the 2 equatorial/3 axial-fluoro amine derivative was only tested against H1N1 and not against the Oseltamivir resistant mutant. Interestingly, the 3Feq 4-amine inactivates H1N1 approximately 20 fold faster than does the 3Fax 4-amine, which is approximately the same ratio as we see for the 3F equatorial versus the 3 axial guanidines on both strains. Accordingly, inactivation by the 3Feq 4-amine is faster than by the 3Fax 4-guanidine. One possible concern was that reactivation (turnover) of the intermediate formed by the 3-F-equatorial compounds would be too fast to be useful. However, while TABLE 21 shows that reactivation is indeed faster, the half lives of 2-4 hours are expected to be sufficient for these compounds to function well in vivo.

As seen above, the 3' equatorial compounds are better at maintaining potency against some viral strains than the 3' axial counterparts. Furthermore, various resistant strains of virus appear to remain sensitive to the 3' equatorial compounds even when sensitivity diminishes for the 3' axial compounds. In addition, the amine is generally expected to have better oral bioavailability than the guanidine.

The enzyme $IC_{50}$ kinetics, reactivation, plaque reduction assays and cross-resistance data all suggest the 4-G3Feq diF SA is a superior inhibitor to the 4-G diF SA. Resistance data also supports the 4-G3Feq SA as having a different resistance profile than Zanamivir, Oseltamivir, and 4-G diF SA. Thus the 3' equatorial F leads to novel interactions of the 4-G group at the ground and transition states, thus avoiding resistance seen with many mutations at E119.

Fluorinated compounds of the class described herein are inhibitors of a range of glycosidases, and specific with respect to their target enzymes. These compounds are mechanism-based in their inhibitory action. They bind to the enzyme like the normal substrate and undergo the first step of catalysis (intermediate formation) like the natural substrate, but then only very slowly undergo the second step (turnover via hydrolysis). Importantly, this mechanism-basis inhibition should make resistance formation by viruses more difficult. Since the inhibitors are mechanism-based, any mutations in the viral enzyme that reduce the inhibition must necessarily reduce the efficiency of the enzyme on the natural substrate. Please note that the sialic acid numbering is different from that of aldose-sugars due to the anomeric carboxylate.

The fluorosialics described herein differ fundamentally from Zanamivir and Oseltamivir in two major ways. Zanamivir and Oseltamivir are reversibly binding inhibitors that interact with the enzyme active site very tightly due to their flattened, cyclic conformation. Their binding mode likely imitates the transition state conformation of the sugar during hydrolysis. They are therefore transition state mimics. The fluorosialics described herein, by contrast, contain no double bond thus adopt a regular chair conformation. They react with the enzyme as if they are substrates and form a covalent bond with the active site nucleophile, and only hydrolyse to products very slowly. They derive their very high efficacies primarily from the long-lived nature of the intermediate formed.

It was not evident that a 3' equatorial F substituent would increase the effectiveness of these compounds against resistant viral strains as compared to stereoisomers having 3' axial F configuration.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention.

REFERENCES

Amaya, M. F., Watts, A., Damager, I., Wehenkel, A., Nguyen, T., Buschiazzo, A., Paris, G., Frasch, A. C., Withers, S. G. and Alzari, P. M. "Structural insights into the catalytic mechanism of *Trypanosoma cruzi* trans-sialidase" (2004) Structure, 12, 775-784.

Bantia S, Parker C D, Ananth S L, Horn L L, Andries K, Chand P, Kotian P L, Dehghani A, El-Kattan Y, Lin T, Hutchison T L, Montgomery J A, Kellog D L, Babu Y S. "Comparison of the anti-influenza virus activity of RWJ-270201 with those of oseltamivir and zanamivir." Antimicrob Agents Chemother. (2001) 45(4):1162-7.

Buchini, S., Buschiazzo, A., Withers, S. G. "Towards a New Generation of Specific *Trypanosoma cruzi* Trans-sialidase Inhibitors" (2008) Angew. Chemie 47, 2700-2703.

Cantarel B L, Coutinho P M, Rancurel C, Bernard T, Lombard V, Henrissat B (2009) "The Carbohydrate-Active EnZymes database (CAZy): an expert resource for Glycogenomics". Nucleic Acids Res 37:D233-238.

Damager, I., Buchini, S., Amaya, M. L., Buschiazzo, A., Alzari, P., Frasch, A. C. Watts, A. Withers, S. G. "Kinetic and Mechanistic Analysis of *Trypanosoma cruzi* Trans-sialidase Reveals a Classical Ping-Pong Mechanism with Acid/Base Catalysis" (2008) Biochemistry, 47, 3507-3512.

Hagiwara et al. "Inhibition of bacterial and viral sialidases by 3-fluoro-N-acetylneuraminic acid" Carbohydrate Research (1994) 263:167-172; and Buchini et al. Agnew. Chem. Int. Ed. (2008) 47:2700-2703.

Henrissat B, Davies G J (1997) "Structural and sequence-based classification of glycoside hydrolases". Curr. Op. Struct. Biol. 7:637-644.

Ikeda, K.; Kitani, S.; Sato, K. Suzuki, T.; Hosokawa, C. Suzuki, Y. Tanaka, K.; Sato, M. "2b,3b-difluoro acid derivatives structurally modified at the C-4 position: synthesis and biological evaluation as inhibitors of human parainfluenza virus type 1" *Carbohydrate Res.* 2004, 339, 1367.

von Itzstein M "The war against influenza: discovery and development of sialidase inhibitors" Nature Reviews Drug Discovery (20076(12): 967-974.

Leneva I A, Goloubeva O, Fenton R J, Tisdale M, Webster R G. "Efficacy of zanamivir against avian influenza A viruses that possess genes encoding H5N1 internal proteins and are pathogenic in mammals." Antimicrob Agents Chemother. (2001) 45(4):1216-24.

Newstead, S., Potter, J. A., Wilson, J. C., Xu, G., Chien, C.-H., Watts, A., Withers, S. G. and Taylor, G. L. "The structure of *Clostridium perfringens* Nani sialidase and its catalytic intermediates" (2008) J. Biol. Chem. 283, 9080-9088.

Tisdale M. "Monitoring of viral susceptibility: new challenges with the development of influenza N A inhibitors." (2000) Rev Med Virol. 10(1):45-55.

Watts, A. G., Oppezzo, P., Withers, S. G., Alzari, P. M. and Buschiazzo, A. "Structural and Kinetic Analysis of two Covalent Sialosyl-Enzyme Intermediates on *Trypanosoma rangeli* Sialidase" (2006) J. Biol. Chem., 281, 4149-4155.

Watts, A. G., Damager, I., Amaya, M. L., Buschiazzo, A., Alzari, P., Frasch, A. C and Withers, S. G. "*Trypanosoma cruzi* Trans-sialidase Operates through a Covalent Sialyl-Enzyme Intermediate: Tyrosine is the Catalytic Nucleophile" (2003) J. Am. Chem. Soc., 125, 7532-7533.

Watts, A. G. and Withers, S. G. "The Synthesis of some Mechanistic Probes for Sialic Acid Processing Enzymes and the Labeling of a Sialidase from *Trypanosoma rangeli*" (2004) Can. J. Chem. 82, 1581-1588.

Withers, S. G. and Aebersold, R. "Approaches to labeling and identification of active site residues in glycosidases" (1995) Protein Science (Invited review) 4, 361-372.

What is claimed is:

1. A compound of formula I:

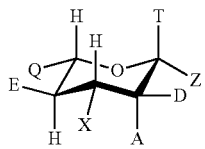

I wherein

T is C(O)NH$_2$, COOH or COOR$^1$,
   wherein R$^1$ is a C$_{1-20}$ linear, branched or cyclic, saturated or unsaturated, optionally substituted alkyl group,
   wherein the optional substituent is selected from one or more of the group consisting of:
   oxo, OH, F, Cl, Br, I, NH$_2$, CN, SH, SO$_3$H and NO$_2$;
Z is F, Cl, Br, or OSO$_2$R$^2$,
   wherein R$^2$ is a C$_{1-20}$ linear, branched or cyclic, saturated or unsaturated, optionally substituted alkyl group,
   wherein the optional substituent is selected from one or more of the group consisting of:
   oxo, OH, F, Cl, Br, I, NH$_2$, CN, SH, SO$_3$H and NO$_2$;
A is selected from the group consisting of: H, F, Cl, Br, OH, CN, OR$^3$, and NO$_2$,
   wherein R$^3$ is a C$_{1-20}$ linear, branched or cyclic, saturated or unsaturated, optionally substituted alkyl group,
   wherein the optional substituent is selected from one or more of the group consisting of:
   oxo, OH, F, Cl, Br, I, NH$_2$, CN, SH, SO$_3$H and NO$_2$;
D is selected from the group consisting of: H, F, Cl, Br, OH, CN, OR$^4$, and NO$_2$, provided A and D are not both H, and
   wherein R$^4$ is a C$_{1-20}$ linear, branched or cyclic, saturated or unsaturated, optionally substituted alkyl group,
   wherein the optional substituent is selected from one or more of the group consisting of:
   oxo, OH, F, Cl, Br, I, NH$_2$, CN, SH, SO$_3$H and NO$_2$;
X is selected from the group consisting of: NH$_2$, NHR$^5$, NHC(NH)NH$_2$, NHC(NH)NHR$^5$, NR$^5$R$^6$, and NHC(NH)N(R$^5$)R$^6$,
   wherein R$^5$ and R$^6$ are independently C$_6$H$_5$, CH$_2$C$_6$H$_5$ or a C$_{1-8}$ alkyl group;
E is selected from the group consisting of: NH$_2$, NHC(O)CH$_3$, OR$^7$, NHR$^7$ and N(R$^7$)(R$^8$),
   wherein R$^7$ and R$^8$ are independently a C$_{1-20}$ linear, branched or cyclic, saturated or unsaturated, optionally substituted alkyl group,
   wherein the optional substituent is selected from one or more of the group consisting of:
   oxo, OH, F, Cl, Br, I, NH$_2$, CN, SH, SO$_3$H and NO$_2$;
Q is selected from the group consisting of: CH$_2$OH, CH$_2$R$^9$, CH(R$^9$)(R$^{10}$), C(R$^9$)(R$^{10}$)(R$^{11}$),

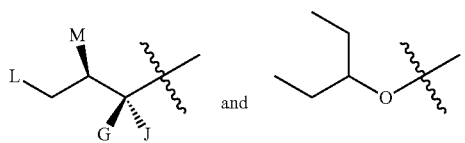

wherein

R$^9$, R$^{10}$ and R$^1$ are independently CH$_3$ or CH$_2$CH$_3$, and
each of J and G is independently selected from the group consisting of: H, OH, OAc, OC(O)CH$_3$, F, Cl, Br, NO$_2$, CN, OR$^{12}$, SO$_2$R$^{12}$, COR$^{12}$ and SR$^{12}$,
   wherein R$^{12}$ is CH$_3$, CH$_2$CH$_3$ or CH$_2$CH$_2$CH$_3$, and
M is H, OH, OAc, OC(O)CH$_3$, NH$_2$, F or Cl, and
L is H, OH, OAc, OC(O)R$^{13}$ or NH$_2$,
   wherein R$^{13}$ is a C$_{1-20}$ linear, branched or cyclic, saturated or unsaturated, optionally substituted alkyl group,
   wherein the optional substituent is selected from one or more of the group consisting of: oxo, OH, F, Cl, Br, I, NH$_2$, CN, SH, SO$_3$H and NO$_2$, or a salt thereof.

2. A compound of formula I:

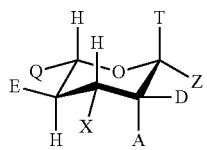

I wherein

T is C(O)NH$_2$, COOH or COOR$^1$,
   wherein R$^1$ is a C$_{1-10}$ linear, branched or cyclic, saturated or unsaturated, optionally substituted alkyl group,
   wherein the optional substituent is selected from one or more of the group consisting of:
   oxo, OH, F, Cl, Br, I, NH$_2$, CN, SH, SO$_3$H and NO$_2$;
Z is F or Cl;
A is F or Cl;
D is H;
X is selected from the group consisting of: NH$_2$, NHCH$_3$, NHCH$_2$CH$_3$, NHCH$_2$CH$_2$CH$_3$, NHCH$_2$CH$_2$CH$_2$CH$_3$, and NHC(NH)NH$_2$;
E is NH$_2$ or NHC(O)CH$_3$;
Q is selected from the group consisting of:

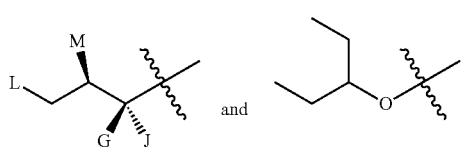

wherein
each of J and G is independently selected from the group consisting of: H, OH, OAc, OC(O)CH$_3$, F, Cl, Br, NO$_2$, CN and OCH$_3$,
M is H, OH, or OAc; and
L is H, OH, or OAc, or a salt thereof.

3. The compound of claim 1, wherein T is COOH or COOR$^1$,
wherein R$^1$ is a C$_{1-20}$ linear, branched or cyclic, saturated or unsaturated, optionally substituted alkyl group,
wherein the optional substituent is selected from one or more of the group consisting of:
oxo, OH, F, Cl, Br, I, NH$_2$, CN, SH, SO$_3$H and NO$_2$.

4. The compound of claim 1, wherein T is C(O)OCH$_3$, C(O)OCH$_2$CH$_3$, C(O)OCH$_2$CH$_2$CH$_3$, C(O)OCH$_2$CH$_2$CH$_2$CH$_3$, C(O)OCH$_2$CH$_2$CH$_2$CH$_2$CH$_3$, C(O)OCH$_2$CH$_2$CH$_2$CH$_2$CH$_2$CH$_3$, C(O)OCH$_2$CH$_2$CH$_2$CH$_2$CH$_2$CH$_2$CH$_3$, or COOH.

5. The compound of claim 1, wherein A is selected from the group consisting of: F, Cl, Br, OH, CN, and NO$_2$.

6. The compound of claim 1, wherein A is selected from the group consisting of: F, Cl, and OR$^3$,
wherein R$^3$ is a C$_{1-20}$ linear, branched or cyclic, saturated or unsaturated, optionally substituted alkyl group,
wherein the optional substituent is selected from one or more of the group consisting of:
oxo, OH, F, Cl, Br, I, NH$_2$, CN, SH, SO$_3$H and NO$_2$.

7. The compound of claim 1, wherein A is F or Cl.

8. The compound of claim 1, wherein A is F.

9. The compound of claim 1, wherein D is selected from the group consisting of: H, F, Cl, Br, OH, CN, and NO$_2$, provided A and D are not both H.

10. The compound of claim 1, wherein D is selected from the group consisting of: H, F, and Cl, provided A and D are not both H.

11. The compound of claim 1, wherein D is F or Cl.

12. The compound of claim 1, wherein D is H, provided A and D are not both H.

13. The compound of claim 1, wherein X is selected from the group consisting of: NH$_2$, NHR$^5$, NHCH$_3$, NHCH$_2$CH$_3$, NHC(NH)NH$_2$, NHC(NH)NHR$^5$, and NR$^5$R$^6$, wherein R$^5$ and R$^6$ are independently C$_6$H$_5$, CH$_2$C$_6$H$_5$ or a C$_{1-8}$ alkyl group.

14. The compound of claim 1, wherein X is selected from the group consisting of: NH$_2$, NHCH$_3$, NHCH$_2$CH$_3$, and NHC(NH)NH$_2$.

15. The compound of claim 1, wherein X is NH$_2$ or NHC(NH)NH$_2$.

16. The compound of claim 1, wherein E is selected from the group consisting of: NH$_2$, NHC(O)CH$_3$, OR$^7$, and NHR$^7$,
wherein R$^7$ is independently a C$_{1-10}$ linear, branched or cyclic, saturated or unsaturated, optionally substituted alkyl group,
wherein the optional substituent is selected from one or more of the group consisting of:
oxo, OH, F, Cl, Br, I, NH$_2$, CN, SH, SO$_3$H and NO$_2$.

17. The compound of claim 1, wherein E is NH$_2$ or NHC(O)CH$_3$.

18. The compound of claim 1, wherein E is NHC(O)CH$_3$.

19. The compound of claim 1, wherein Q is selected from the group consisting of: CH$_2$R$^9$, CH(R$^9$)(R$^{10}$), C(R$^9$)(R$^{10}$)(R$^{11}$),

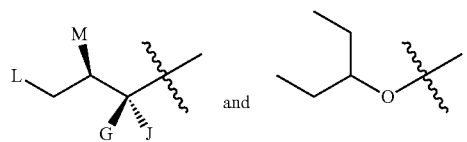

wherein
R$^9$, R$^{10}$ and R$^{11}$ are independently CH$_3$ or CH$_2$CH$_3$, and
each of J and G is independently selected from the group consisting of: H, OH, OAc, OC(O)CH$_3$, F, Cl, Br, NO$_2$, CN, OR$^{12}$, SO$_2$R$^{12}$, COR$^{12}$ and SR$^{12}$,
wherein R$^{12}$ is CH$_3$, CH$_2$CH$_3$ or CH$_2$CH$_2$CH$_3$, and
M is H, OH, OAc, OC(O)CH$_3$, NH$_2$, F or Cl, and
L is H, OH, OAc, OC(O)R$^{13}$ or NH$_2$,
wherein R$^{13}$ is a C$_{1-10}$ linear, branched or cyclic, saturated or unsaturated, optionally substituted alkyl group, and
wherein the optional substituent is selected from one or more of the group consisting of:
oxo, OH, F, Cl, Br, I, NH$_2$, CN, SH, SO$_3$H and NO$_2$.

20. The compound of claim 1, wherein Q is selected from the group consisting of:

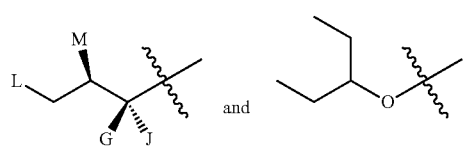

wherein
each of J and G is independently selected from the group consisting of: H, OH, OAc, OC(O)CH$_3$, F, Cl, Br, NO$_2$, CN and OCH$_3$,
M is H, OH, OAc, OC(O)CH$_3$, NH$_2$, F or Cl, and
L is H, OH, OAc, OC(O)R$^{13}$ or NH$_2$,
wherein R$^{13}$ is CH$_3$, CH$_2$CH$_3$ or CH$_2$CH$_2$CH$_3$.

21. The compound of claim 1, wherein Q is selected from the group consisting of:

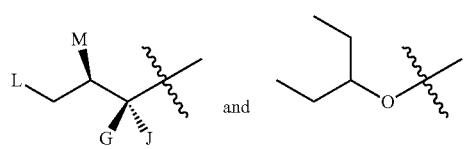

wherein
each of J and G is independently selected from the group consisting of: H, OH, and OAc,
M is H, OH, or OAc, and
L is H, OH, or OAc.

22. The compound of claim 1, wherein Q is:

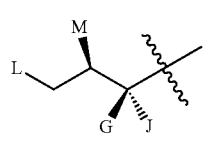

wherein
each of J and G is independently selected from the group consisting of: H, OH, and OAc, M is H, OH, or OAc, and
L is H, OH, or OAc.

23. The compound of claim 1, wherein Q is:

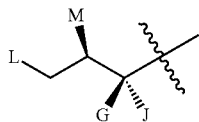

wherein
each of J and G is independently selected from the group consisting of: H, OH, and OAc,
M is OH, or OAc, and
L is OH, or OAc.

24. A pharmaceutical composition comprising a compound according to claim 1 or a pharmaceutically acceptable salt thereof and a pharmaceutically acceptable excipient.

25. A pharmaceutical composition comprising a compound according to claim 14 or a pharmaceutically acceptable salt thereof and a pharmaceutically acceptable excipient.

26. A pharmaceutical composition comprising a compound according to claim 16 or a pharmaceutically acceptable salt thereof and a pharmaceutically acceptable excipient.

27. A pharmaceutical composition comprising a compound according to claim 20 or a pharmaceutically acceptable salt thereof and a pharmaceutically acceptable excipient.

28. A method of modulating viral neuraminidase activity, the method comprising contacting a viral neuraminidase with one or more compounds described in claim 1 or a pharmaceutically acceptable salt thereof.

29. The method of claim 28, wherein the viral neuraminidase is a GH34 neuraminidase.

30. The method of claim 28, wherein the modulation of viral neuraminidase activity comprises contacting the compound or the pharmaceutically acceptable salt thereof to an animal and is effective to treat influenza in the animal.

31. The method of claim 30 wherein the animal is a human.

* * * * *